USO11865729B2

(12) United States Patent
Larkin et al.

(10) Patent No.: US 11,865,729 B2
(45) Date of Patent: *Jan. 9, 2024

(54) TOOL POSITION AND IDENTIFICATION INDICATOR DISPLAYED IN A BOUNDARY AREA OF A COMPUTER DISPLAY SCREEN

(71) Applicant: Intuitive Surgical Operations, Inc., Sunnyvale, CA (US)

(72) Inventors: David Q. Larkin, Menlo Park, CA (US); Thomas R. Nixon, San Jose, CA (US); David S. Mintz, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 702 days.

This patent is subject to a terminal disclaimer.

(21) Appl. No.: 16/921,995

(22) Filed: Jul. 7, 2020

(65) Prior Publication Data

US 2020/0331147 A1 Oct. 22, 2020

Related U.S. Application Data

(63) Continuation of application No. 15/638,172, filed on Jun. 29, 2017, now Pat. No. 10,730,187, which is a (Continued)

(51) Int. Cl.
*A61B 34/20* (2016.01)
*A61B 34/10* (2016.01)
(Continued)

(52) U.S. Cl.
CPC ........... *B25J 9/1692* (2013.01); *A61B 1/0005* (2013.01); *A61B 1/00009* (2013.01);
(Continued)

(58) Field of Classification Search
CPC ......... A61B 34/10; A61B 34/20; A61B 34/25; A61B 34/30; A61B 34/37; A61B 34/74; A61B 90/37
See application file for complete search history.

(56) References Cited

U.S. PATENT DOCUMENTS 3,628,535 A 12/1971 Ostrowsky et al.
3,818,284 A 6/1974 DeVersterre et al.
(Continued)

FOREIGN PATENT DOCUMENTS

CA 2682992 A1 11/2008
CN 1846181 A 10/2006
(Continued)

OTHER PUBLICATIONS

Office Action dated Oct. 24, 2019 for Korean Application No. 1020197022941 filed May 11, 2011, 14 pages.
(Continued)

*Primary Examiner* — John R Downey
(74) *Attorney, Agent, or Firm* — Haynes & Boone, LLP.

(57) ABSTRACT

An apparatus comprises a memory device and a processor coupled to a display device, an image capture device, and the memory device. The processor is configured to: cause images captured by the image capture device to be displayed in a viewing area on the display device; determine a position of a tool in a reference frame of the image capture device; determine a position to display a non-depictive symbol for the tool in a boundary area circumscribing the viewing area to indicate a direction of the determined position of the tool relative to a field of view of the image capture device, by determining a trajectory of the tool; and cause the non-depictive symbol to be displayed at the determined position
(Continued)

in the boundary area while images that were captured by the image capture device are restricted to being displayed in the viewing area.

13 Claims, 10 Drawing Sheets

Related U.S. Application Data continuation of application No. 11/478,531, filed on Jun. 29, 2006, now Pat. No. 9,718,190.

(51) Int. Cl.
| | | |
|---|---|---|
| *B25J 9/16* | (2006.01) | |
| *A61B 17/00* | (2006.01) | |
| *A61B 1/00* | (2006.01) | |
| *A61B 90/00* | (2016.01) | |
| *A61B 1/005* | (2006.01) | |
| *A61B 34/30* | (2016.01) | |
| *A61B 1/313* | (2006.01) | |
| *A61B 34/00* | (2016.01) | |
| *A61B 34/37* | (2016.01) | |

(52) U.S. Cl.
CPC .......... *A61B 1/0051* (2013.01); *A61B 1/3132* (2013.01); *A61B 17/00234* (2013.01); *A61B 34/10* (2016.02); *A61B 34/20* (2016.02); *A61B 34/25* (2016.02); *A61B 34/30* (2016.02); *A61B 34/37* (2016.02); *A61B 34/74* (2016.02); *A61B 90/36* (2016.02); *A61B 90/37* (2016.02); *B25J 9/1694* (2013.01); *B25J 9/1697* (2013.01); *A61B 90/361* (2016.02); *A61B 2017/00199* (2013.01); *A61B 2017/00292* (2013.01); *A61B 2017/00296* (2013.01); *A61B 2034/102* (2016.02); *A61B 2034/107* (2016.02); *A61B 2034/2057* (2016.02); *A61B 2034/2065* (2016.02); *A61B 2034/301* (2016.02); *A61B 2034/741* (2016.02); *A61B 2034/742* (2016.02); *A61B 2090/365* (2016.02); *A61B 2090/367* (2016.02); *A61B 2090/371* (2016.02); *A61B 2090/373* (2016.02); *G05B 2219/39449* (2013.01); *G05B 2219/40607* (2013.01); *G05B 2219/45123* (2013.01)

(56) References Cited

U.S. PATENT DOCUMENTS

| | | |
|---|---|---|
| 3,890,552 A | 6/1975 | Devol et al. |
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,673,988 A | 6/1987 | Jansson et al. |
| 4,722,056 A | 1/1988 | Roberts et al. |
| 4,759,074 A | 7/1988 | Iadipaolo et al. |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | Labiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,891,767 A | 1/1990 | Rzasa et al. |
| 4,942,539 A | 7/1990 | Mcgee et al. |
| 4,979,949 A | 12/1990 | Matsen, III et al. |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor et al. |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A | 2/1997 | Miyagi |
| 5,617,858 A | 4/1997 | Taverna et al. |
| 5,624,390 A | 4/1997 | Van Dyne |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |

(56) References Cited

U.S. PATENT DOCUMENTS

| | | |
|---|---|---|
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green et al. |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 5,999,662 A | 12/1999 | Burt et al. |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,358,749 B1 | 3/2002 | Orthman |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,434,416 B1 | 8/2002 | Mizoguchi et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,491,701 B2 | 12/2002 | Tierney et al. |
| 6,493,608 B1 | 12/2002 | Niemeyer et al. |
| 6,522,906 B1 | 2/2003 | Salisbury, Jr. et al. |
| 6,522,908 B1 | 2/2003 | Miyashita et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,656,110 B1 | 12/2003 | Irion et al. |
| 6,659,939 B2 | 12/2003 | Moll et al. |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,702,736 B2 | 3/2004 | Chen et al. |
| 6,714,839 B2 | 3/2004 | Salisbury, Jr. et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,866,671 B2 | 3/2005 | Tierney et al. |
| 6,876,891 B1 | 4/2005 | Schuler et al. |
| 6,899,672 B2 | 5/2005 | Chin et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,118,582 B1 | 10/2006 | Wang et al. |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,211,978 B2 | 5/2007 | Chang et al. |
| 7,297,142 B2 | 11/2007 | Brock |
| 7,302,288 B1 | 11/2007 | Schellenberg et al. |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,833,156 B2 | 11/2010 | Williams et al. |
| 7,865,266 B2 | 1/2011 | Moll et al. |
| 7,963,913 B2 | 6/2011 | Devengenzo et al. |
| 7,967,813 B2 | 6/2011 | Cooper et al. |
| 7,979,157 B2 | 7/2011 | Anvari |
| 7,996,110 B2 | 8/2011 | Lipow et al. |

(56) References Cited

U.S. PATENT DOCUMENTS

| | | |
|---|---|---|
| 7,998,058 B2 | 8/2011 | Kura et al. |
| 8,004,229 B2 | 8/2011 | Nowlin et al. |
| 8,005,571 B2 | 8/2011 | Sutherland et al. |
| 8,016,749 B2 | 9/2011 | Clerc et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,142,447 B2 | 3/2012 | Cooper et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,244,443 B2 | 8/2012 | Oshima et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,419,717 B2 | 4/2013 | Diolaiti et al. |
| 8,541,970 B2 | 9/2013 | Nowlin et al. |
| 8,554,368 B2 | 10/2013 | Fielding et al. |
| 8,597,280 B2 | 12/2013 | Cooper et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,801,601 B2 | 8/2014 | Prisco et al. |
| 8,816,628 B2 | 8/2014 | Nowlin et al. |
| 8,823,308 B2 | 9/2014 | Nowlin et al. |
| 8,864,652 B2 | 10/2014 | Diolaiti et al. |
| 8,864,751 B2 | 10/2014 | Prisco et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,259,283 B2 | 2/2016 | Ogawa et al. |
| 9,333,042 B2 | 5/2016 | Diolaiti et al. |
| 9,345,387 B2 | 5/2016 | Larkin |
| 9,387,048 B2 | 7/2016 | Donhowe et al. |
| 9,469,034 B2 | 10/2016 | Diolaiti et al. |
| 9,492,927 B2 | 11/2016 | Diolaiti et al. |
| 9,516,996 B2 | 12/2016 | Diolaiti et al. |
| 9,565,990 B2 | 2/2017 | Lee et al. |
| 9,622,826 B2 | 4/2017 | Diolaiti et al. |
| 9,629,520 B2 | 4/2017 | Diolaiti |
| 9,717,563 B2 | 8/2017 | Tognaccini et al. |
| 9,718,190 B2 | 8/2017 | Larkin et al. |
| 9,788,909 B2 | 10/2017 | Larkin et al. |
| 9,789,608 B2 | 10/2017 | Itkowitz et al. |
| 9,795,446 B2 | 10/2017 | Dimaio et al. |
| 9,801,690 B2 | 10/2017 | Larkin et al. |
| 9,901,408 B2 | 2/2018 | Larkin |
| 9,949,798 B2 | 4/2018 | Weir et al. |
| 9,956,044 B2 | 5/2018 | Gomez et al. |
| 10,008,017 B2 | 6/2018 | Itkowitz et al. |
| 10,137,575 B2 | 11/2018 | Itkowitz et al. |
| 10,188,472 B2 | 1/2019 | Diolaiti et al. |
| 10,258,425 B2 | 4/2019 | Mustufa et al. |
| 10,271,909 B2 | 4/2019 | Guthart et al. |
| 10,271,912 B2 | 4/2019 | Diolaiti et al. |
| 10,271,915 B2 | 4/2019 | Diolaiti et al. |
| 10,282,881 B2 | 5/2019 | Itkowitz et al. |
| 10,368,952 B2 | 8/2019 | Tognaccini et al. |
| 10,433,919 B2 | 10/2019 | Guthart et al. |
| 10,507,066 B2 | 12/2019 | Dimaio et al. |
| 10,537,994 B2 | 1/2020 | Diolaiti et al. |
| 10,695,136 B2 | 6/2020 | Larkin |
| 10,730,187 B2 | 8/2020 | Larkin et al. |
| 10,737,394 B2 | 8/2020 | Itkowitz et al. |
| 10,772,689 B2 | 9/2020 | Gomez et al. |
| 10,773,388 B2 | 9/2020 | Larkin et al. |
| 10,828,774 B2 | 11/2020 | Diolaiti et al. |
| 10,959,798 B2 | 3/2021 | Diolaiti et al. |
| 10,984,567 B2 | 4/2021 | Itkowitz et al. |
| 11,382,702 B2 | 7/2022 | Tognaccini et al. |
| 11,389,255 B2 | 7/2022 | DiMaio et al. |
| 11,399,908 B2 | 8/2022 | Diolaiti et al. |
| 11,432,888 B2 | 9/2022 | Diolaiti et al. |
| 11,596,490 B2 | 3/2023 | Diolaiti et al. |
| 11,638,622 B2 | 5/2023 | Mustufa et al. |
| 11,638,999 B2 | 5/2023 | Itkowitz et al. |
| 2001/0035871 A1 | 11/2001 | Bieger et al. |
| 2002/0044104 A1 | 4/2002 | Friedrich et al. |
| 2002/0045888 A1 | 4/2002 | Ramans et al. |
| 2002/0089544 A1 | 7/2002 | Jahn et al. |
| 2002/0120188 A1 | 8/2002 | Brock et al. |
| 2002/0128552 A1 | 9/2002 | Nowlin et al. |
| 2002/0156345 A1 | 10/2002 | Eppler et al. |
| 2002/0193800 A1 | 12/2002 | Kienzle et al. |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0060927 A1 | 3/2003 | Gerbi et al. |
| 2003/0109780 A1 | 6/2003 | Coste-Maniere et al. |
| 2003/0114730 A1 | 6/2003 | Hale et al. |
| 2003/0144649 A1 | 7/2003 | Ghodoussi et al. |
| 2003/0167103 A1 | 9/2003 | Tang et al. |
| 2003/0225479 A1 | 12/2003 | Waled |
| 2004/0024311 A1 | 2/2004 | Quaid et al. |
| 2004/0034283 A1 | 2/2004 | Quaid et al. |
| 2004/0039485 A1 | 2/2004 | Niemeyer et al. |
| 2004/0044295 A1 | 3/2004 | Reinert et al. |
| 2004/0046711 A1 | 3/2004 | Triebfuerst |
| 2004/0046916 A1 | 3/2004 | Lyu et al. |
| 2004/0049205 A1 | 3/2004 | Lee et al. |
| 2004/0077940 A1 | 4/2004 | Kienzle et al. |
| 2004/0106916 A1 | 6/2004 | Quaid et al. |
| 2004/0138700 A1 | 7/2004 | Cooper et al. |
| 2004/0176751 A1 | 9/2004 | Weitzner et al. |
| 2004/0189675 A1 | 9/2004 | Pretlove et al. |
| 2004/0210105 A1 | 10/2004 | Hale et al. |
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0096892 A1 | 5/2005 | Watanabe et al. |
| 2005/0107680 A1 | 5/2005 | Kopf et al. |
| 2005/0113640 A1 | 5/2005 | Saadat et al. |
| 2005/0166413 A1 | 8/2005 | Crampton et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2005/0273198 A1 | 12/2005 | Bischoff |
| 2006/0013523 A1 | 1/2006 | Childlers et al. |
| 2006/0058988 A1 | 3/2006 | Defranoux et al. |
| 2006/0079108 A1 | 4/2006 | McCoy |
| 2006/0142657 A1 | 6/2006 | Quaid et al. |
| 2006/0149129 A1 | 7/2006 | Watts et al. |
| 2006/0161045 A1 | 7/2006 | Merril et al. |
| 2006/0161138 A1 | 7/2006 | Orban et al. |
| 2006/0178559 A1 | 8/2006 | Kumar et al. |
| 2006/0258938 A1 | 11/2006 | Hoffman et al. |
| 2006/0261770 A1 | 11/2006 | Kishi et al. |
| 2006/0293592 A1 | 12/2006 | Jensen |
| 2007/0016174 A1 | 1/2007 | Millman et al. |
| 2007/0021738 A1 | 1/2007 | Hasser et al. |
| 2007/0038080 A1 | 2/2007 | Salisbury et al. |
| 2007/0060879 A1 | 3/2007 | Weitzner et al. |
| 2007/0071310 A1 | 3/2007 | Kobayashi et al. |
| 2007/0081714 A1 | 4/2007 | Wallack et al. |
| 2007/0106307 A1 | 5/2007 | Bodduluri et al. |

(56) References Cited

U.S. PATENT DOCUMENTS

| | | |
|---|---|---|
| 2007/0135803 A1 | 6/2007 | Belson |
| 2007/0138992 A1 | 6/2007 | Prisco et al. |
| 2007/0142825 A1 | 6/2007 | Prisco et al. |
| 2007/0142968 A1 | 6/2007 | Prisco et al. |
| 2007/0144298 A1 | 6/2007 | Miller |
| 2007/0151389 A1 | 7/2007 | Prisco et al. |
| 2007/0156019 A1 | 7/2007 | Larkin et al. |
| 2007/0156285 A1 | 7/2007 | Sillman et al. |
| 2007/0167801 A1 | 7/2007 | Webler et al. |
| 2007/0177009 A1 | 8/2007 | Bayer et al. |
| 2007/0197896 A1 | 8/2007 | Moll et al. |
| 2007/0229015 A1 | 10/2007 | Yoshida et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287889 A1 | 12/2007 | Mohr |
| 2007/0287992 A1 | 12/2007 | Diolaiti et al. |
| 2007/0296366 A1 | 12/2007 | Quaid et al. |
| 2007/0299387 A1 | 12/2007 | Williams et al. |
| 2008/0033240 A1 | 2/2008 | Hoffman et al. |
| 2008/0045800 A2 | 2/2008 | Farr |
| 2008/0051629 A1 | 2/2008 | Sugiyama et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin et al. |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0081992 A1 | 4/2008 | Kagermeier |
| 2008/0118115 A1 | 5/2008 | Williamson et al. |
| 2008/0119824 A1 | 5/2008 | Weitzner et al. |
| 2008/0140087 A1 | 6/2008 | Barbagli |
| 2008/0151041 A1 | 6/2008 | Shafer et al. |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0269862 A1 | 10/2008 | Elmouelhi et al. |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz Morales |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326322 A1 | 12/2009 | Diolaiti |
| 2009/0326552 A1 | 12/2009 | Diolaiti |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0298839 A1 | 11/2010 | Castro |
| 2010/0317965 A1 | 12/2010 | Itkowitz et al. |
| 2010/0328363 A1 | 12/2010 | Nakanishi |
| 2010/0331855 A1 | 12/2010 | Zhao et al. |
| 2010/0331856 A1 | 12/2010 | Carlson et al. |
| 2010/0332033 A1 | 12/2010 | Diolaiti et al. |
| 2011/0071675 A1 | 3/2011 | Wells et al. |
| 2011/0196199 A1 | 8/2011 | Donhowe et al. |
| 2011/0258568 A1 | 10/2011 | Pandurangan et al. |
| 2011/0290856 A1 | 12/2011 | Shelton, IV et al. |
| 2011/0313573 A1 | 12/2011 | Schreiber et al. |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0245375 A1 | 9/2013 | Dimaio et al. |
| 2013/0289767 A1 | 10/2013 | Lim et al. |
| 2013/0289768 A1 | 10/2013 | Yeung et al. |
| 2014/0052150 A1 | 2/2014 | Taylor et al. |
| 2015/0032126 A1 | 1/2015 | Nowlin et al. |
| 2015/0051733 A1 | 2/2015 | Nowlin et al. |
| 2017/0209232 A1 | 7/2017 | Larkin et al. |
| 2017/0210012 A1 | 7/2017 | Larkin et al. |
| 2017/0305016 A1 | 10/2017 | Larkin et al. |
| 2018/0206924 A1 | 7/2018 | Gomez et al. |
| 2018/0297206 A1 | 10/2018 | Larkin et al. |
| 2019/0047154 A1 | 2/2019 | Itkowitz et al. |
| 2019/0090967 A1 | 3/2019 | Guthart et al. |
| 2019/0110847 A1 | 4/2019 | Diolaiti et al. |
| 2019/0201134 A1 | 7/2019 | Diolaiti et al. |
| 2019/0201152 A1 | 7/2019 | Diolaiti et al. |
| 2019/0209262 A1 | 7/2019 | Mustufa et al. |
| 2019/0213770 A1 | 7/2019 | Itkowitz et al. |
| 2019/0298463 A1 | 10/2019 | Tognaccini et al. |
| 2020/0085520 A1 | 3/2020 | Dimaio et al. |
| 2020/0094400 A1 | 3/2020 | Diolaiti |
| 2020/0368915 A1 | 11/2020 | Itkowitz et al. |
| 2021/0059780 A1 | 3/2021 | Sutherland et al. |
| 2021/0153964 A1 | 5/2021 | Diolaiti et al. |
| 2021/0256749 A1 | 8/2021 | Itkowitz et al. |
| 2021/0290326 A1 | 9/2021 | Diolaiti et al. |
| 2022/0296317 A1 | 9/2022 | Dimaio et al. |
| 2022/0354600 A1 | 11/2022 | Tognaccini et al. |
| 2022/0361969 A1 | 11/2022 | Diolaiti et al. |
| 2023/0225803 A1 | 7/2023 | Mustufa et al. |

FOREIGN PATENT DOCUMENTS

| | | |
|---|---|---|
| CN | 1879574 A | 12/2006 |
| CN | 101160104 A | 4/2008 |
| CN | 101184429 A | 5/2008 |
| CN | 101193603 A | 6/2008 |
| CN | 101291635 A | 10/2008 |
| CN | 101530347 A | 9/2009 |
| CN | 101594816 A | 12/2009 |
| CN | 101610712 A | 12/2009 |
| CN | 102170835 A | 8/2011 |
| EP | 514584 A2 | 11/1992 |
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| EP | 1269389 B1 | 9/2005 |
| EP | 1131004 B1 | 10/2009 |
| JP | H01280449 A | 11/1989 |
| JP | H01310875 A | 12/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08224241 A | 9/1996 |
| JP | H08275958 A | 10/1996 |
| JP | H08299363 A | 11/1996 |
| JP | H09141580 A | 6/1997 |
| JP | H10146341 A | 6/1998 |
| JP | H11309 A | 1/1999 |

(56) References Cited

FOREIGN PATENT DOCUMENTS

| | | |
|---|---|---|
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 3539645 B2 | 7/2004 |
| JP | 2004223128 A | 8/2004 |
| JP | 3587830 B2 | 11/2004 |
| JP | 2005110878 A | 4/2005 |
| JP | 2005135278 A | 5/2005 |
| JP | 2005515012 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007531553 A | 11/2007 |
| JP | 2008173724 A | 7/2008 |
| JP | 2008544814 A | 12/2008 |
| JP | 2009006410 A | 1/2009 |
| JP | 2009012106 A | 1/2009 |
| JP | 2009039814 A | 2/2009 |
| JP | 2009512514 A | 3/2009 |
| JP | 2009525097 A | 7/2009 |
| JP | 4354042 B2 | 10/2009 |
| JP | 2009537229 A | 10/2009 |
| JP | 2009539573 A | 11/2009 |
| JP | 2009542362 A | 12/2009 |
| JP | 2011525845 A | 9/2011 |
| JP | 4883563 B2 | 2/2012 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-9823216 A1 | 6/1998 |
| WO | WO-0030548 A1 | 6/2000 |
| WO | WO-03061482 A1 | 7/2003 |
| WO | WO-2004014244 A2 | 2/2004 |
| WO | WO-2004114037 A2 | 12/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2006124390 A2 | 11/2006 |
| WO | WO-2007005555 A2 | 1/2007 |
| WO | WO-2007012185 A1 | 2/2007 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008065581 A2 | 6/2008 |
| WO | WO-2008094766 A2 | 8/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |
| WO | WO-2010040685 A1 | 4/2010 |

OTHER PUBLICATIONS

3D Slicer, http://slicer.org/welcome.html, downloaded Oct. 25, 2006, p. 1; and Introduction, http:/slicer.org/intro/index.html, downloaded Oct. 25, 2006, pp. 1-4.

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18-Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Arun, K.S et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew R.S., et al., "Ground Control Testbed for Space Station Freedom Robot Manipulators," IEEE Virtual Reality Annual International Symposium, 1993, pp. 69-75.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total , Morgan kaufmann publishers, Inc.

Bartels, Richard H et al., "Solution of the Matrix Equation AX+XB=C," Communications of the ACM, 1972, pp. 820-826, vol. 15—Issue 9, ACM Press.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K et al., "Controlling Remote Manipulators through Kinesthetic Coupling," Computers in Mechanical Engineering, 1983, pp. 48-60, vol. 1—Issue 1.

Ben Gayed, M. et al., "An Advanced Control Micromanipulator for Surgical Applications," Systems Science, 1987, pp. 123-134, vol. 13.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

(56) References Cited

OTHER PUBLICATIONS

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

Boctor, Emad, M. et al., "CISUS: An integrated 3D ultrasound system for IGT using a modular tracking API," Proceedings of the SPIE, 2004, pp. 247-256, vol. 5367, SPIE.

Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, p. 46, vol. 6-Supplement 1, Taylor & Francis Health Science.

Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science-Part II, Lecture Notes in Computer Science, 2001, pp. 13-22, vol. 2074, Springer.

Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.

Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.

Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.

Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.

Borovoi, A.V., "Stability of a manipulator with force feedback," Izv. AN SSSR Mekhanika Tverdogo Teal, 1990, pp. 37-45, vol. 25—Issue 1, Allerton Press, Inc.

Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.

Brown, Myron M. et al., "Advances in Computational Stereo," IEEE Transactions on Pattern Analysis and Machine Intelligence (PAMI), 2003, pp. 993-1008, vol. 25 Issue, IEEE.

Burdea, Grigore et al., "Dextrous Telerobotics with Force Feedback—an overview. Part 2: Control and Implementation," Robotica, 1991, pp. 291-298, vol. 9.

Burschka, Darius et al., "Navigating Inner Space: 3-D Assistance for Minimally Invasive Surgery," Robotics and Autonomous Systems, 2005, pp. 5-26, vol. 52—Issue 1, Elsevier.

Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.

Burschka, Darius et al., "Scale-Invariant Registration of Monocular Endoscopic Images to CT-Scans for Sinus Surgery," Med Image Anal, 2004, pp. 413-421, vol. 2, Springer-Verlag.

Burschka, Darius et al., "Scale-Invariant Registration of Monocular Stereo Images to 3D Surface Models," IEEE Int. Conf. on Robots and Systems, 2004, pp. 2581-2586, vol. 3, IEEE.

Bzostek, Andrew et al., "A Testbed System for Robotically Assisted Percutaneous Pattern Therapy," Medical Image Computing and Computer-Assisted Surgery, Lecture Notes In Computer Science, 1999, pp. 1098-1107, vol. 1679, Springer.

Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes In Computer Science, 1997, pp. 299-308, vol. 1205, Springer-Verlag.

Bzostek, Andrew, "Computer-Integrated needle therapy systems: Implementation and Analysis," Computer Science, 2005, 379 pages.

Bzostek, Andrew, "Image Guided Percutaneous Pattern Placement in Soft Tissue," The Johns Hopkins University Dept. of Computer Science: Baltimore, 1997, pp. Jan. 22, 2007.

Cadeddu, Jeffrey A. et al., "A Robotic System for Percutaneous Renal Access," The Journal of Urology, 1997, pp. 1589-1593, vol. 158—Issue 4.

Cadeddu, Jeffrey et al., "A robotic system for percutaneous renal access incorporating a remote center of motion design," Journal of Endourolog, 1998, S237, vol. 12.

Cannon, Jeremy W. et al., "Real-time three-dimensional ultrasound for guiding surgical tasks," Computer Aided Surgery, 2003, pp. 82-90, vol. 8—No. 2, John Wiley & Sons.

Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.

Carr, J., "Surface reconstruction in 3D medical imaging," PhD Thesis, Part 1, University of Canterbury, Christchurch, New Zealand, 1996, 112 Pages.

Carr, J., "Surface reconstruction in 3D medical imaging," PhD Thesis, Part 2, University of Canterbury, Christchurch, New Zealand, 1996, 112 Pages.

Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.

Chang, Jun Keun et al., "Intravascular micro active catheter for minimal invasive surgery," 1st Annual International Conference on Microtechnologies in Medicine and Biology, 2000, pp. 243-246.

Chen, Homer H. "A Screw Motion Approach to Uniqueness Analysis of Head-Eye Geometry," Computer Vision and Pattern Recognition, 1991, pp. 145-151, IEEE.

Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.

Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.

Choti, Michael A., "Hepatic Radiofrequency Ablation," Cancer Journal, 2000, pp. S291-S292, vol. 6—issue 4, Jones and Bartlett.

Choti, Michael A., "Surgical Management of Hepatocellular Carcinoma: Resection and Ablation," Journal of Vascular and Interventional Radiology, 2002, pp. S197-S203, vol. 13—No. 9.

(56) References Cited

OTHER PUBLICATIONS

Christensen, B. et al., "Model based sensor directed remediation of underground storage tanks," International Conf. on Robotics and Automation, Sacramento, CA, Apr. 1991, pp. 1377-1383, vol. 2. IEEE.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

Chung, Mathew et al., "Laparascopic Radiofrequency Ablation of Unresectable Hepatic Malignancies," Surg Endosc, 2001, pp. 1020-1026, vol. 15—No. 9, Springer-Verlag.

Cleary, Kevin et al., "State of the Art in Surgical Robotics:Clinical Applications and Technology Challenges," Computer Aided Surgery, 2001 [retrieved on Feb. 24, 2002], pp. 1-26.

Cleary, Kevin et al., "State of the art surgical robotics clinical applications and technology challenges," Computer Aided Surgery, 2001, pp. 312-328, vol. 6; PART 6, John Wiley & Sons.

Cleary,K. et al., "Robotically-assisted spine nerve blocks," Radiology, 2001, 1 page, vol. 221—No. 618.

Colgate J.E., "Power and Impedance Scaling in Bilateral Manipulation," IEEE International Conference on Robotics and Automation, Sacramento, California, Apr. 1991, vol. 3, pp. 2292-2297.

D'Angelica M., "Staging Laparoscopy for Potentially Respectable Noncolorectal," Ann Surg Oncol, 2002, pp. 204-209, vol. 9—No. 2, Lippincott Williams & Wilkins.

Daniilidis, Konstantinos, Hand-Eye Calibration Using Dual Quaternions, Int. J. of Robotics Research, 1999, pp. 286-298, vol. 18 (3), Sage Publications, Inc.

Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.

Davies, S.C., et al., "Ultrasound Quantitaion of Respiratory Organ Motion in the Upper Abdomen," British Journal of Radiology, Nov. 1994, vol. 67 (803), pp. 1096-1102.

De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.

Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.

Degoulange, E. et al., "HIPPOCRATE: an intrinsically safe robot for medical applications," IEEE/RSH International Conference on Intelligent Biomedicine, 1998, pp. 959-964, vol. 2, IEEE.

Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No 1, IEEE.

Dewan, Maneesh et al., "Vision-Based Assistance for Ophthalmic Micro-Surgery," Proceedings of Seventh International Conference on Medical Image Computing and Computer- Assisted Intervention (MICCAI), 2004, pp. 49-57, vol. 3217, Springer-Verlag.

Dodds, Zachary et al., "A hierarchical architecture for vision-based robotic manipulation tasks," in Proceedings of the International Conference on Vision Systems, 1999, pp. 312-330, vol. 542, Springer-Verlag.

Doggett, Stephen W., "Image Registered Real Time Intra-Operative Treatment Planning: Permanent Seed Brachytherapy," 2000, pp. 4.

Dolan, J.M. et al., "A Robot in an Operating Room: A Bull in a China Shop?," IEEE Proceedings of the Ninth Annual Conference of the IEEE Engineering in Medicine and Biology Society, Nov. 1987, vol. 2, pp. 1096-1097.

Elder, Matthew C. et al., "Specifying user interfaces for safety critical medical systems," Second Annual International Symposium on Medical Robotics and Computer Assisted Surgery, Nov. 1995, pp. 148-155.

Eldridge, B. et al., "A Remote Center of Motion Robotic Arm for Computer Assisted Surgery," Robotica, 1996, pp. 103-109, vol. 14 Issue 1.

Ellsmere, James et al., "A navigation system for augmenting laparoscopic ultrasound," Medical Image Computing and Computer-Assisted Intervention, Lecture Notes in Computer Science, 2003, pp. 184-191, Springer.

Extended European Search Report for Application No. 12847686.8 dated Jul. 27, 2015, 7 pages.

Extended European Search Report for Application No. 12848026.6 dated Jul. 29, 2015, 8 pages.

Extended European Search Report for Application No. 16173584.0, dated Dec. 12, 2016, 5 pages.

Extended European Search Report for Application No. EP11150208, dated Feb. 17, 2014, 5 pages.

Fattal, Lischinsk, "Variational Classification for Visualization of 3D Ultrasound Data," Proceedings of the conference on Visualization, 2001, pp. 403-410, IEEE Computer Society.

Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.

Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.

Fichtinger, Gabor et al., "Robotically Assisted Percutaneous Local Therapy and Biopsy," 10th International Conference of Advance Robotics, 2001, pp. 133-151, IEEE.

Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.

Fichtinger, Gabor et al., "System For Robotically Assisted Prostate Biopsy and Therapy With intraOperative CT Guidance," Journal of Academic Radiology, 2002, pp. 60-74, vol. 9 No 1, Elsevier.

Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.

Fisher, Scott S., "Virtual interface environment," IEEE/A1AA 7th Digital Avionics Systems Conference Ft. Worth Texas, 1986, pp. 346-350, IEEE.

Frantz D.D et al., "Accuracy assessment protocols for electromagnetic tracking systems," Physics in Medicine and Biology, 2003, pp. 2241-2251, Issue 48.

Fu, K.S. et al., "Robotics: control, sensing, vision, and intelligence," 1987, pp. 12-76 and 201-265, Ch. 2 & 5, McGraw-Hill Book Company.

Fuchs, Henry et al., "Augmented Reality Visualization for Laparoscopic Surgery," Medical Image Computing and Computer-Assisted Intervention, 1998, pp. 934-943, vol. 1496, Springer-Verlag.

Fukuda, Toshio et al., "A new method of master-slave type of teleoperation for a micro-manipulator system," IEEE Microrobots and Teleoperations Workshop, 1987, 5 pages, IEEE.

Funda J., et al., "An experimental user interface for an interactive surgical robot," In 1st International Symposium on Medical Robotics and Computer Assisted Surgery (MRCAS 94), 1994, pp. 196-203.

Funda J., et al., "Constrained Cartesian Motion Control for Teleoperated Surgical Robots," IEEE Transactions on Robotics and Automation, IEEE, Jun. 1996, vol. 12 (3), pp. 453-465.

Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.

Funda, Janez et al., "Control and evaluation of a 7-axis surgical robot for laparoscopy," IEEE Int. Conf. on Robotics and Automation, 1995, pp. 1477-1484, vol. 2, IEEE.

Funda, Janez et al., "Image-Guided Command and Control of a Surgical Robot," Proc. Medicine Meets Virtual Reality II, 1994, pp. 52-57.

(56) References Cited

OTHER PUBLICATIONS

Funda, Janez et al., "Optimal Motion Control for Teleoperated Surgical Robots," Intl. Symp. on Optical Tools for Manuf. & Adv Autom, Telemanipulator Technology and Space Telerobotics, 1993, pp. 211-222, vol. 2057, SPIE.
Furuta, Katsuhisa et al., "Master slave manipulator based on virtual internal model following control concept," IEEE Intl. Conference on Robotics and Automation, 1987, pp. 567-572, vol. 1, IEEE.
Ganssle J.G.,,A Guide to Debouncing, The Ganssle Group,Jun. 2008,26 pages.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, A., et al., Table of Contents for"Applied Optimal Estimation," The Analytic Science Corporation, MIT Press, Cambridge, Massachusetts, 1974, 4 pages.
Gennari, G. et al., "Probabilistic data association methods in visual tracking of groups," IEEE Conference on Computer Vision and Pattern Recognition, 2004, pp.I-790-1-797, vol. 1—issue. 27, IEEE.
Gigot, Jean-Francois et al., "Laparoscopic Liver Resection for Malignant Liver Tumors Prelimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Green, Philip, S. et al., "Mobile telepresence surgery," 2nd Annual Intl Symposium on Med. Robotics and Computer Assisted Surgery, Maryland Nov. 1995, pp. 97-103.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager G., et al., "The X Vision System: A Portable Substrate for Real Time Vision Applications," Computer Vision and Image Understanding, 1998, vol. 69 (1),pp. 23-37.
Hager Gregory D. et al., "Multiple Kernel Tracking with SSD," Proceedings of the IEEE Conference on Computer Vision and Pattern Recognition (CVPR 2004), 2004, pp. 1-790-1-797, vol. 1—issue 27, IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager, Gregory D., "A Modular System for Robust Positioning Using Feedback from Stereo Vision," IEEE Transactions on Robotics and Automation, Aug. 1997, vol. 13 (4), pp. 582-595.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "A robotic procedure for transurethral resection of the prostate," Second Annual International Symposium on Medical Robotics and Computer Assisted Surgery, 1995, pp. 264-271.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline A.J., et al., "Image-Guided Surgery: Preliminary Feasibility Studies of Frameless Stereotactic Liver Surgery," Archives of Surgery, 1999, vol. 134 (6), pp. 644-650.
Herline, Alan J. et al., "Surface Registration for Use in Interactive," Image-Guided Liver Surgery, Computer Aided Surgery, 2000, pp. 11-17, vol. 5—No. 2.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Herman, Barry C., et al., "Telerobotic surgery creates opportunity for augmented reality surgery," Abstract No. T1F2, Telemedicine Journal and E-Health, vol. 11, Issue 2, p. 203, Apr. 2005.
Herper Matthew, "Watch a $1.5 Million Surgical Robot Play a Board Game," Forbes. Apr. 12, 2011. 2 pages, Online [Available: http://www.forbes.com/sites/matthewherper/2011/04/12/watch-a-1-5-million-surgical-robot-play-a-board-game/#587224f011f5] Accessed Jun. 7, 2016.
Hespanha J.P., et al., "What Tasks Can Be Performed with an Uncalibrated Stereo Vision System," International Journal of Computer Vision, Nov. 1999, vol. 35 (1), 33 pages.
Hill J.W., et al., "Telepresence surgery demonstration system," IEEE International Conference on Robotics and Automation, 1994, vol. 3, pp. 2302-2307.
Ho, S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Preliminary Examination Report for Application No. PCT/US00/08526, dated Jun. 29, 2001, 4 pages.
International Preliminary Report on Patentability for Application No. PCT/US09/56078, dated Sep. 3, 2010, 19 pages.
International Search Report and Written Opinion for Application No. PCT/US2012/064379, dated Mar. 29, 2013, 12 pages.
International Search Report and Written Opinion for Application No. PCT/US2012/064400, dated Mar. 27, 2013, 10 pages.
International Search Report for application No. PCT/US00/08526, dated Jul. 14, 2000, 2 pages.
International Search Report for application No. PCT/US99/29145, dated May 15, 2000, 1 page.
Intuitive Surgical, Inc., "Intuitive Surgical daVinci API v5.0 Reference Manual," generated Jul. 17, 2006, 149 pages.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.

(56) References Cited

OTHER PUBLICATIONS

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Johns Hopkins University and Intuitive Surgical, Inc., "System Requirements for the Surgical Assistant Workstation," Rev. 2, Jan. 29, 2007, 17 pages.
Jones D.B. et al., Chapter 25, "Next-Generation 3D Videosystems may Improve Laparoscopic Task Performance," Interactive Technology and the New Paradigm for Healthcare, 1995, pp. 152-160.
Joskowicz L., et al., "Computers in Imaging and Guided Surgery," Computing in Science and Engineering, 2001, vol. 3 (5), pp. 65-72.
Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.
Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor A., et al., "Simple Biomanipulation Tasks with "Steady Hand" Cooperative Manipulator," Lecture Notes in Computer Science, 2003, vol. 2878, pp. 141-148.
Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.
Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.
Kapoor, Ankur et al., "Suturing in Confined Spaces: Constrained Motion Control of a Hybrid 8-DOF Robot," Proceedings, 12th International Conference on Advanced Robotics, 2005, pp. 452-459.
Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.
Kato H., et al. "Virtual Object Manipulation on a Table-Top AR Environment," Hiroshima City University, 2000, 9 pages.
Kato H., et al., "The Effects of Spatial Cues in Augmented Reality Video Conferencing," Hiroshima City University, Aug. 2001, 4 pages.
Kavoussi L.R., "Laparoscopic Donor Neptarectomy," Kidney International, 2000, vol. 57, pp. 2175-2186.
Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H. , "Human Extenders," ASME J. Dynamic Systems, Measurements and Control, 1993, pp. 281-290, vol. 115 No. 2(B).
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Design and analysis of the statically balanced direct-drive robot manipulator," Robotics and Computer-Integrated Manufacturing, 1989, pp. 287-293, vol. 6, Issue 4.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kilmer, R. D. et al., "Watchdog safety computer design and implementation," RI/SME Robots 8 Conference, Jun. 1984, pp. 101-117.
Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.
Kitagawa, Masaya et al., "Effect of Sensory Substitution on Suture Manipulation Forces for Surgical Teleoperation," 12th Annual Medicine Meets Virtual Reality Conference, 2005, 8 pages.
Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Kragic D. et al., "Human-Machine Collaborative Systems for Microsurgical Applications," International Symposium on Robotics Research, 2005, pp. 731-741, vol. 24—Issue 9, Sage Publications.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention-Part , Lecture Notes In Computer Science, 2002, pp. 9-16, vol. 2488, Springer Verlag.
Kumar R., "An Augmented Steady Hand System for Precise Micromanipulation," PhD thesis in Computer Science, The Johns Hopkins University, Baltimore, Apr. 2001, 118 pages.
Kumar, R., et al., "An Augmentation System for Fine Manipulation," Proceedings of the Third International Conference on Medical Image Computing and Computer-Assisted Intervention, Lecture Notes In Computer Science, 2000, vol. 1935, pp. 957-965.
Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes In Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lacroute, P., "The VolPack vol. Rendering Library," 1995, information downloaded from https://graphics.stanford.edu/software/volpack/, 4 pages.
Lacroute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.

(56) References Cited

OTHER PUBLICATIONS

Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.
Lavonius, Maija I. et al., "Staging of Gastric Cancer: A Study with Spiral Computed Tomography, Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.
Lawson, Charles L. et al., "Linear least squares with linear inequality constraints Solving Least Squares Problems," 1974, pp. 158-173, Prentice Hall Inc.
Lazarevic, Zoran, "Feasibility of a Stewart Platform with Fixed Actuators as a Platform for CABG Surgery Device," 1997, 45 pages, Master's Thesis Columbia University Department of Bioengineering.
Lee Jr, F.T., et al., "CT-monitored Percutaneous Cryoablation in a Pig Liver Model: Pilot Study," Radiology, 1999, vol. 211 (3), pp. 687-692.
Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.
Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.
Levoy, Marc, "Display of Surfaces from Volume Data," IEEE Computer Graphics and Applications, 1988, pp. 29-37, vol. 8—Iss. 3, IEEE.
Li, M., "Intelligent Robotic Surgical Assistance for Sinus Surgery," Ph.D. Dissertation, Johns Hopkins University, Baltimore, Aug. 2005, 246 pages.
Li, Ming and Russell H. Taylor, "Performance of surgical robots with automatically generated spatial virtual fixtures," IEEE International Conference on Robotics and Automation, Barcelona, Spain, Apr. 2005, pp. 217-222.
Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.
Li, Ming et al., "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.
Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.
Li, Ming et al., "Recognition of Operator Motions for Real-Time Assistance using Virtual Fixtures," IEEE, Haptics 2003, 11th Symposium on Haptic Interfaces for Virtual Environment and Teleoperator Systems, Mar. 22-23, 2003, pp. 125-131, IEEE.
Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.
Loser, Michael H. et al., "Visual servoing for automatic and uncalibrated percutaneous procedures," SPIE Medical Imaging, 2000, pp. 270-281, vol. 3976, SPIE.
Lunwei Z., et al., "FBG Sensor Devices for Spatial Shape Detection of Intelligent Colonoscope," IEEE International Conference on Robotics and Automation, Apr. 2004, New Orleans, Louisiana, pp. 835-840.
Madhani A.J., "Design of Teleoperated Surgical Instruments for Minimally Invasive Surgery," Feb. 1998, 251 pages.
Maehara, S. et al., "Laparoscopy-Assisted Hepatectomy Using the Endoclose," Surgical Endoscopy, 2002, vol. 16 (9), pp. 1363-1364.
Maier, Georg, E. et al., "A Dynamically Configurable General Purpose Automation Controller," Proceedings of IFAC/IFIP Symp. on Software for Computer Control, 1986, pp. 47-52, Pergamon Press.
Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.
Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.
Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.
Masamune K., et al., "Development of a MRI Compatible Needle Insertion Manipulator for Stereotactic Neurosurgery," Journal of Image Guided Surgery, 1995, vol. 1, pp. 242-248.
Masamune K., et al., "System for Robotically Assisted Percutaneous Procedures With Computed Tomography Guidance," Journal of Computer-Assisted Surgery, 2001, vol. 6 (6), pp. 370-383.
Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.
Masamune, Ken et al., "Development of a MRI Compatible Needle Insertion Manipulator for Stereotactic Neurosurgery," Image Guid Surg, 1995, pp. 165-172.
Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.
Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.
Mayer, Hermann et al., "Skill Transfer and Learning by Demonstration in a Realistic Scenario of Laparoscopic Surgery," International Conference on Humanoids, 2003, 17 pages, IEEE.
Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.
Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes In Computer Science, 2001, pp. 343-350, vol. 2208, Springer-Verlag.
Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.
Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.
Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.
Michael B. Cohn's Home Page http://www.bsac.eecs.berkeley.edu/users/michaelc/, downloaded Nov. 1, 1996, p. 1; UC Berkeley/Endorobotics Corporation Surgical Robotics Project Job Openings,

(56) References Cited

OTHER PUBLICATIONS http://www.bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.
Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.
Mitsuishi M., et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part 1, Lecture Notes In Computer Science, 2002, pp. 25-34, vol. 2488, Springer-Verlag.
Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.
Nakakura, Eric K et al., "Hepatocellular Carcinoma: Current Management Recommendations," Advances on Oncology, 2000, pp. 12-18, vol. 16—No. 2.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Novotny Paul M. et al., "Tool Localization in 3D Ultrasound Images," Medical Image Computing and Computer-Assisted Intervention, 2003, pp. 969-970, vol. 2879, Springer.
Office Action dated May 1, 2012 for Japanese Application No. 20090518470 filed Jun. 22, 2007, 7 pages.
Office Action dated Aug. 3, 2016 for Chinese Application No. 201280055140.8 filed Nov. 9, 2012, 9 pages.
Office Action dated Sep. 3, 2014 for Chinese Application No. 2010823529 filed Mar. 26, 2010, 8 pages.
Office Action dated Jan. 4, 2016 for European Application No. 10717330.4 filed Mar. 26, 2010, 8 pages.
Office Action dated Jun. 4, 2010 for European Application No. EP07784512.1 filed Jun. 22, 2007, 5 pages.
Office Action dated Jan. 5, 2009 for European Application No. 20060784595 filed Jun. 5, 2006, 2 pages.
Office Action dated Jul. 6, 2016 for Japanese Application No. 2015202607 filed Oct. 14, 2015, 7 pages.
Office Action dated Apr. 7, 2014 for Japanese Application No. 20130133899 filed Jun. 26, 2013, 2 page.
Office Action dated May 7, 2015 for European Application No. 20090770698 filed Jun. 4, 2009, 5 pages.
Office Action dated May 9, 2016 for Chinese Application No. 201410779062.7 filed Jun. 4, 2009, 13 pages.
Office Action dated May 9, 2016 for Korean Application No. 10-2011-7025321 filed Oct. 26, 2011, 18 pages.
Office Action dated Dec. 10, 2015 for Chinese Application No. 201280055123.4 filed Nov. 9, 2012, 19 pages.
Office Action dated Feb. 12, 2015 for Chinese Application No. 2010823529 filed Mar. 26, 2010, 6 pages.
Office Action dated Jan. 12, 2012 for Japanese Application No. 20080515812 filed Jun. 5, 2005, 5 pages.
Office Action dated Jun. 12, 2015 for Japanese Application No. 20130186992 filed Sep. 10, 2013, 8 pages.
Office Action dated Feb. 13, 2015 for Japanese Application No. 20140086093 filed Apr. 18, 2014, 1 page.
Office Action dated Sep. 13, 2016 for Japanese Application No. 2014-541317 filed Nov. 9, 2012, 8 pages.
Office Action dated Jul. 14, 2013 for Japanese Application No. 20120503535 filed Mar. 26, 2010, 3 pages.
Office Action dated Dec. 15, 2015 for Korean Application No. 10-2010-7027491 filed Dec. 7, 2010, 14 pages.
Office Action dated Dec. 16, 2016 for Japanese Application No. 2015242062 filed Oct. 14, 2015, 13 pages.
Office Action dated Jun. 19, 2014 for Japanese Application No. 20110272384 filed Dec. 13, 2011, 3 pages.
Office Action dated Nov. 19, 2013 for Chinese Application No. 2006820112 filed Jun. 5, 2006, 9 pages.
Office Action dated Jun. 20, 2013 for Japanese Application No. 20110272385 filed Dec. 13, 2011, 5 pages.
Office Action dated Jun. 20, 2013 for Japanese Application No. 20110272386 filed Dec. 13, 2011, 8 pages.
Office Action dated Jun. 20, 2013 for Japanese Application No. JP20110272384 filed Dec. 13, 2011, 7 pages.
Office Action dated Jan. 21, 2014 for Chinese Application No. 2010823529 filed Mar. 26, 2010, 44 pages.
<span style="font-family: calibri;">Office Action dated Nov. 22, 2016 for Japanese Application No. 2014-541311 filed Nov. 9, 2012, 16 pages.
Office Action dated Jul. 24, 2013 for Korean Application No. 20087030829 filed Dec. 18, 2008, 11 pages.
Office Action dated Mar. 24, 2014 for Japanese Application No. 20120503535 filed Mar. 26, 2010, 13 pages.
Office Action dated Jan. 26, 2015 for Japanese Application No. 20130186992 filed Sep. 10, 2013, 9 pages.
Office Action dated Dec. 27, 2013 for Japanese Application No. 20110272384 filed Dec. 13, 2011, 5 pages.
Office Action dated Dec. 27, 2013 for Japanese Application No. 20110272386 filed Dec. 13, 2011, 8 pages.
Office Action dated Feb. 27, 2013 for Japanese Application No. 20090518470 filed Jun. 22, 2007, 5 pages.
Office Action dated Jan. 28, 2016 for Korean Application No. 10-2011-7006578 filed Mar. 22, 2011, 9 pages.
Office Action dated Nov. 29, 2013 for Japanese Application No. 20120503535 filed Mar. 26, 2010, 11 pages.
Office Action dated Apr. 30, 2015 for European Application No. 20100724228 filed Jun. 11, 2010, 5 pages.
Office Action dated Nov. 30, 2015 for Chinese Application No. 201280055140.8 filed Nov. 9, 2012, 12 pages.
Office Action dated Aug. 31, 2011 for Japanese Application No. 20080515812 filed Jun. 5, 2005, 10 pages.
Office Action dated Jul. 31, 2014 for Japanese Application No. 2013-194017 filed Sep. 19, 2013.
Office Action dated May 31, 2016 for Korean Application No. 10-2012-7000713 filed Jan. 10, 2012, 12 pages.
Ohbuchi R., et al., "Incremental Volume Reconstruction and Rendering for 3D Ultrasound Imaging," The International Society of Optical Engineering, 1992, vol. 1808, pp. 312-323.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu A., et al., "Motion-based Robotic Instrument Targeting under C-Arm Fluoroscopy," Medical Image Computing and Computer-Assisted Interventions, 2000, vol. 1935, pp. 988-998.
Paul, Howard A. et al., "Development of a Surgical Robot for Cementless Total Hip Arthroplasty," Clinical Orthopaedics, Dec. 1992, pp. 57-66, vol. 285.

(56) References Cited

OTHER PUBLICATIONS

Payandeh S., et al., "On Application of Virtual Fixtures as an Aid for Telemanipulation and Training," Proceedings 10th Symposium on Haptic Interfaces for Virtual Environment and Teleoperator Systems (HAPTICS), Mar. 2002, pp. 18-23.
PCT/US06/21852 International Search Report dated Nov. 2, 2006, 3 pages.
PCT/US06/21852 Written Opinion of the International Search Authority dated Nov. 2, 2006, 6 pages.
PCT/US06/40754 International Search Report dated Jul. 11, 2007, 4 pages.
PCT/US06/40754 Written Opinion of the International Search Authority dated Apr. 23, 2008, 8 pages.
PCT/US07/71850 International Search Report and Written Opinion of the International Searching Authority, dated Feb. 13, 2008, 9 pages.
PCT/US09/46234 International Search Report and Written Opinion of the International Searching Authority, dated Sep. 9, 2009, 13 pages.
PCT/US09/56078 International Search Report and Written Opinion of the International Searching Authority, dated Jan. 20, 2010, 12 pages.
PCT/US10/28886 International Search Report and Written Opinion of the International Searching Authority, dated Jul. 6, 2010, 11 pages.
PCT/US10/28897 International Search Report and Written Opinion of the International Searching Authority, dated Jul. 19, 2010, 16 pages.
PCT/US10/38246 International Search Report and Written Opinion of the International Searching Authority, dated Sep. 14, 2010, 17 pages.
PCT/US2011/036109 International Search Report and Written Opinion of the International Searching Authority, dated Oct. 19, 2011, 16 pages.
PCT/US2011/036109 Invitation to Pay Additional Fees and Partial International Search Report, dated Aug. 18, 2011, 5 pages.
Podnos Y.D., et al., "Laparoscopic Ultrasound with Radiofrequency Ablation in Cirrhotic Patients with Hepatocellular Carcinoma: Technique and Technical Considerations," American Surgeon, Dec. 2001, vol. 67 (12), pp. 1181-1184.
Pose—definition from Merriam Webster Dictionary, 4 pages, [online], [retrieved on Apr. 3, 2015]. Retrieved from the Internet:< URL: http://www.merriam-webster.com/dictonary/pose>.
Posture—definition from Merriam Webster Dictionary, 4 pages, [online], [retrieved on Apr. 3, 2015]. Retrieved from the Internet:< URL: http://www.merriam-webster.com/dictonary/posture>.
Poulose B.K., et al., "Human vs Robotic Organ Retraction During Laparoscopic Nissen Fundoplication," Surgical Endoscopy, 1999, vol. 13, pp. 461-465.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI, Lecture Notes in Computer Science, 2003, pp. 279-286, vol. I, Springer.
Prasad, Srinivas K. et al., "A minimally invasive approach to pelvic osteolysis," 2002, in Proc. Computer-Assisted Orthopaedic Surgery (CAOS), pp. 349-350.
Pre-Appeal Examination Report, dated Sep. 3, 2014 for Japanese Application No. JP20120503535 filed Mar. 26, 2010, 7 pages.
Preising B., et al., "A Literature Review: Robots in Medicine," IEEE Engineering in Medicine and Biology, Jun. 1991, vol. 10(2), pp. 13-22.
Ramey, N. A., "Stereo-Based Direct Surface Tracking with Deformable Parametric Models," Thesis submitted to The Johns Hopkins University, Maryland, Apr. 2003, 104 pages.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al., "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging", Digestive Surgery, 2002, pp. 479-483, vol. 19—No. 6.
Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.
Rohling, Robert et al., "Three-dimensional spatial compounding of ultrasound images," Medical Image Analysis, 1996, pp. 177-193, vol. 1—No. 3, Oxford University Press.
Rohling, Robert N. et al., "Radial basis function interpolation for 3-d ultrasound," CUED/F-INFENG/TR 327, Cambridge University, Jul. 1998, 28 Pages.
Rosen J., et al., "The BlueDRAGON—A System for Measuring the Kinematics and the Dynamics of Minimally Invasive Surgical Tools In-Vivo," Proceedings of the 2002 IEEE International Conference on Robotics & Automation, 2002, pp. 1876-1881.
Rosenberg, Louis B., "Human interface hardware for virtual laparoscopic surgery," Proceedings of the Interactive Technology and the New Paradigm for Healthcare, 1995, pp. 322-325, Amsterdam: IOS Press.
Rosenberg, Louis B., "Virtual Fixtures: Perceptual Tools for Telerobotic Manipulation," IEEE Virtual Reality International Symposium, 1993, pp. 76-82, IEEE.
Rothbaum Daniel L. et al., "Robot-assisted stapedotomy: micropick fenestration of the stapes footplate," Otolaryngology—Head and NeckSurgery, 2002, pp. 417-426, vol. 127.
Rothbaum Daniel L. et al., "Task Performance in stapedotomy: Comparison between surgeons of different experience levels," Otolaryngology—Head and Neck Surgery, 2003, pp. 71-77, vol. 128—No. 1.
Roy, Jaydeep, "Advances in the design, analysis and control of force controlled robots," Master's Thesis, Mechanical Engineering, Johns Hopkins University, Baltimore, 2001, 210 Pages.
Sakas, Georgios et al., "Extracting surfaces from fuzzy 3D-Ultrasound data," Proceedings of the 22nd annual conference on Computer graphics and interactive techniques, 1995, pp. 465-474.
Salcudean, Septimiu E. et al., "A Robot System for Medical Ultrasound," 9th International Symposium of Robotics Research (ISRR'99), 1999, pp. 195-202.
Santambrogio, R. et al., "Ultrasound-Guided Interventional Procedures of the Liver During Laparoscopy: Technical Considerations," Surg Endosc, 2002, pp. 349-354, Springer-Verlag.
Sastry S., "MilliRobotics in Minimally Invasive Telesurgery," Retrieved from Internet [URL: http://robotics.eecs.berkeley.edu] 1995, 3 pages.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, http://robotics.eecs.berkeley.edu, Nov. 1, 1995, Total 8 pages.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Schorr, O., et al., "Distributed Modular Computer-Integrated Surgical Robotic Systems: Architecture for Intelligent Object Distribution," Proceedings of the Third International Conference on

(56) References Cited

OTHER PUBLICATIONS

Medical Image Computing and Computer-Assisted Intervention, Lecture Notes In Computer Science, 2000, vol. 1935, pp. 979-987.
Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.
Schweikard, Achim et al., "Motion Planning in Stereotaxic Radiosurgery," IEEE Transactions on Robotics and Automation, 1993, pp. 909-916, vol. 1, IEEE.
Scott D.J., et al., "Accuracy and Effectiveness of Laparoscopic vs Open Hepatic Radiofrequency Ablation," Surgical Endoscopy, Feb. 2001, vol. 15 (2),pp. 135-140.
Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.
Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.
Solomon S.B., et al., "Robotically Driven Interventions: A Method of Using CT Fluoroscopy without Radiation Exposure to the Physician," Radiology, 2002, vol. 225, pp. 277-282.
Solus-3D Ultrasound Project in Obstetrics and Gynaecology, University of Cambridge, http://mi.eng.cam.ac.uk/research/projects/Solus/, downloaded Jul. 5, 2007, 4 pages.
Sommer, Graham et al., "Liver tumors: utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.
Stetten, George D et al., "Overlaying Ultrasound Images on Direct Vision," Journal of Ultrasound in Medicine, 2001, pp. 235-240, vol. 20—No. 3.
Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.
Stoainovici D., et al., "Robotic Telemanipulation for Percutaneous Renal Access," In 16th World Congress on Endourology, New York City, Sep. 3-6, 1998, Poster Session 17-5, pp. S201.
Stoianovici, Dan et al., "Robotic For Precise Percutaneous Needle Insertion," In Thirteenth Annual Meeting of the Society for Urology and Engineering. San Diego, May 1998, pp. 4.
Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.
Stoll, Jeff, "Ultrasound-based servoing of manipulators for telesurgery," Telemanipulator and Telepresence Technologies VIII Conference, 2001, pp. 78-85, SPIE.
Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.
Supplementary European Search Report for Application No. EP00919930, dated May 9, 2003, 7 pages.
Supplementary Partial European Search Report for Application No. EP19990966064, dated Jun. 12, 2007, 3 pages.
Suramo, I. et al., "Cranio-caudal movements of the liver, pancreas and kidneys in respiration," Acta Radiologica: Diagnosis, 1984, pp. 129-131, vol. 25, Radiological Societies.
Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.
Taubes, Gary et al., "Surgery in Cyberspace," Discover magazine, Dec. 1994, vol. 15, issue 12, pp. 85-92.
Tavakoli, M., et al., A Force Reflective Master-Slave System for Minimally Invasive Surgery, Proc. IEEE/RSJ International Conference on Intelligent Robots and Systems, 2003, pp. 3077-3082, vol. 4, IEEE.
Taylor R., et al., "A Telerobotic System for Augmentation of Endoscopic Surgery," in IEEE Conference on Engineering in Medicine and Biology, 1992, vol. 14, pp. 1054-1056.
Taylor R.H. et al., "Medical Robotics and Computer-Integrated Surgery," Chapter 52 in Springer Handbook of Robotics, Springer, 2008, pp. 1199-1222.
Taylor R.H., et al., "A Computational Architecture for Programmable Automation Research," Intelligent Robots and Computer Vision, 1986, vol. 726, pp. 438-440.
Taylor R.H., et al., Table of Contents, "Computer-Integrated Surgery," Technology and Clinical Applications, The MIT Press, Cambridge, MA, 1996, 8 pages.
Taylor, R.H., "Medical Robotics and Computer-Integrated Surgery," Handbook of Industrial Robotics, Second Edition, 1999, pp. 1213-1227, Chapter 65, John Wiley & Sons.
Taylor, R.H., et al., "A General Purpose Control Architecture for Programmable Automation Research," Proceedings of the Third International Symposium on Robotics, 1986, pp. 165-173, MIT Press.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. "Medical Robots," in Computer and Robotic Assisted Knee and Hip Surgery, 2004, pp. 54-59, Oxford Press.
Taylor, Russell H. "The Planning and Execution of Straight Line Manipulator Trajectories," IBM Journal of Research and Development, 1979, pp. 424-436, vol. 23—Issue 4.
Taylor, Russell H. and Christopher Hasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "An Image-directed Robotic System for Hip Replacement Surgery," J. Robotics Society of Japan, 1990, pp. 615-620, vol. 8—issue 5.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Medical Robotics in Computer-Integrated Surgery," IEEE Transactions on Robotics md Automation, 2003, pp. 765-781, vol. 19—No. 5, IEEE.

(56) References Cited

OTHER PUBLICATIONS

Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell H., "A Perspective on Medical Robotics," Proceedings of the IEEE, vol. 94, No. 9, Sep. 2006, pp. 1652-1664.
Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.
Taylor, Russell H., "Ultrasound Assistant for a Laparoscopic Surgical Robot," NIH STTR Phase II Proposal R42-RR019159, revised May 2001, 54 pages.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell, H. et al., "A Steady-Hand Robotic System for Microsurgical Augmentation," International Journal of Robotics Research, 1999, pp. 1201-1210, vol. 18—No. 12, Springer- Verlag.
Taylor, Russell, H. et al., "AML A Manufacturing Language," The International Journal of Robotics Research, 1982, pp. 19-41, vol. 1—No. 3, SAGE Publications.
Taylor, Russell, H et al., "The Architecture of an Integrated Robot System," First Int. Conf. on Advanced Robotics (ICAR)., 1983, pp. 389-398.
Taylor, Russell, H. et al., "An Integrated Robot Systems Architecture," Proceedings of the IEEE, 1983, pp. 842-856, vol. 71—Issue 7, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572, vol. 60—No. 4, Elsevier.
Thring, M.W., "Robots and Telechirs: Manipulators with Memory; Remote Manipulators; Machine Limbs for the Handicapped," Ellis Horwood Limited, England, 1983, 79 pages, including Table of Contents, Preface, Chap. 5 (pp. 108-131), Chap. 7 (pp. 194-195, 235), Chap. 8 (pp. 236-278), Chap. 9 (p. 279).
Toon, John, "Virtual Reality for Eye Surgery," Georgia Tech Research News, 1993, 4 Pages.
Toyama, Kentaro et al., "Incremental Focus of Attention for Robust Vision-based Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.

U.S. Appl. No. 11/583,963 Non-Final Office Action dated Jul. 9, 2009, 40 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master-Slave Robots," Motor-con, MOTORCON'87, Hannover, Apr. 1987, pp. 309-316.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster R.J. et al., "Nonholonomic Modeling of Needle Steering," The International Journal of Robotics Research, 2006, vol. 25 (5-6), pp. 509-525.
Webster Robert J. et al., "Design Considerations for Robotic Needle Steering," International Conference on Robotics and Automation, 2005, pp. 3588-3594, IEEE.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Wei, Zhouping et al."Robot-assisted 3D-TRUS guided prostate brachytherapy: system integration and validation," Medical Physics, 2004, pp. 539-548, vol. 31—No. 3.
Wengert, C., "Camera Calibration Toolbox for Matlab," http://www.vision.caltech.edu/bouguetj/calib_doc/, downloaded Oct. 24, 2006, 9 pages.
Wilhelm, Dirk et al., "Electromagnetically Navigated Laparoscopic Ultrasound," Surg. Technol. Int, 2003, pp. 50-54, vol. 11.
Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.
Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.
Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.
Yamagata H., et al., "Development of a New Display Method for Compound 3D Ultrasound Images: Fusion 3D Images From B-mode and 3D Doppler Images," 1999, vol. 70, pp. 43-46.
Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.
Yao, Jianhua et al., "Deformable registration between a statistical born density atlas and X-ray images," Second International Conference on Computer Assisted Orthopaedic Surgery, 2002, pp. 168-169.
Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.
Zacherl, Johannes et al., "Current value of intraoperative sonography during surgery for hepatic neoplasms," World J Surg, 2002, pp. 550-554, vol. 26—No. 5.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Zhang, Z., "A Flexible New Technique for Camera Calibration," Technical report MSR-TR-98-71, Microsoft Research, Microsoft Corporation, Redmond, WA, Dec. 1998, pp. 1-21.
Azuma et al., "Recent Advances in Augmented Reality," IEEE Computer Graphics and Applications, Dec. 2001, 14 pages.
Lievin et al., "Stereoscopic Augmented Reality System for Computer Assisted Surgery," CARS 2001, Jun. 27-30, 2001, 5 pages.
Office Action dated Nov. 29, 2019 for U.S. Appl. No. 15/638,172, filed Jun. 29, 2017, 11 pages.

(56) References Cited

OTHER PUBLICATIONS

Extended European Search Report for Application No. EP21158299.4 dated May 21, 2021, 09 pages.

TOOL POSITION AND IDENTIFICATION INDICATOR DISPLAYED IN A BOUNDARY AREA OF A COMPUTER DISPLAY SCREEN

CROSS REFERENCE TO RELATED APPLICATIONS

This application is a continuation application of U.S. patent application Ser. No. 15/638,172 (filed Jun. 29, 2017), now U.S. Pat. No. 10,730,187, which is a continuation application of U.S. patent application Ser. No. 11/478,531 (filed Jun. 29, 2006), now U.S. Pat. No. 9,718,190, each of which is incorporated herein by reference in their entirety.

FIELD OF THE INVENTION

The present invention generally relates to robotic surgical systems and in particular, to a tool position and identification indicator displayed in a boundary area of a computer display screen.

BACKGROUND

Robotic surgical systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using robotic surgical systems is strong and growing.

One example of a robotic surgical system is the da Vinci® Surgical System from Intuitive Surgical, Inc., of Sunnyvale, California. The da Vinci® system includes a surgeon's console, a patient-side cart, a high performance 3-D vision system, and Intuitive Surgical's proprietary EndoWrist™ articulating instruments, which are modeled after the human wrist so that when added to the motions of the robot arm holding the surgical instrument, they allow a full six degrees of freedom of motion, which is comparable to the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

A stereoscopic endoscope is positioned near a surgical site to capture left and right views for display on the stereoscopic video display. When an instrument is outside a viewing area on the display, however, the surgeon may not know how far away or in which direction the instrument is at the time. This makes it difficult for the surgeon to guide the instrument to the surgical site. Also, it may be disconcerting to the surgeon if the instrument unexpectedly appears in view. Even when an instrument is within the viewing area of the display, the surgeon may not know which instrument it is or which patient-side manipulator (e.g., robotic arm on the patient-side cart) the instrument is associated with. This makes it difficult, for example, for the surgeon to instruct a patient side assistant to replace the instrument with another during a surgical procedure.

In order to locate an instrument which is outside of a viewing area on the display, it may be necessary to move the endoscope until the instrument appears in the viewing area. In this case, if the surgical instrument is being guided to the surgical site, the cameras' zoom and focus controls may also require frequent adjustment, making the process tedious and time consuming for the surgeon. If it happens that the instrument is in the camera field of view ("FOV"), but outside of the viewing area, because of a zoom-in adjustment to the view, then a zoom-out adjustment may be performed so that the instrument is back in the viewing area. Such a zoom-out, however, may be undesirable when a delicate surgical procedure is being performed that requires close scrutiny by the surgeon.

OBJECTS AND BRIEF SUMMARY

Accordingly, one object of various aspects of the present invention is a method for indicating a tool position relative to images being displayed on a computer display screen when the tool is outside a viewing area of the screen.

Another object of various aspects of the present invention is a method for indicating a tool distance from images being displayed on a computer display screen when the tool is outside a viewing area of the screen.

Another object of various aspects of the present invention is a method for indicating a tool orientation relative to images being displayed on a computer display screen when the tool is outside a viewing area of the screen.

Another object of various aspects of the present invention is a method for indicating a tool position or orientation relative to images being displayed on a computer display screen when the tool is occluded within a viewing area of the screen.

Still another object of various aspects of the present invention is a method for indicating a tool identification on a computer display screen that clearly identifies which patient-side manipulators are connected to which surgical instruments, so as to improve surgeon performance and surgeon-assistant communications.

These and additional objects are accomplished by the various aspects of the present invention, wherein the embodiments of the invention are summarized by the claims that follow below.

In preferred embodiments of the method, apparatus and medical robotic system, the symbol provides information identifying the tool and/or its associated patient-side manipulator by an associated color or some other means, such as text or numeric information that is written on or displayed adjacent to the symbol. In the latter case, the text information may be continuously displayed on the computer display screen. Alternatively, it may only be displayed when a cursor is placed over the symbol or the symbol is clicked on using a pointing device.

Additional objects, features and advantages of the various aspects of the present invention will become apparent from the following description of its preferred embodiment, which description should be taken in conjunction with the accompanying drawings.

DETAILED DESCRIPTION

Figure 1:
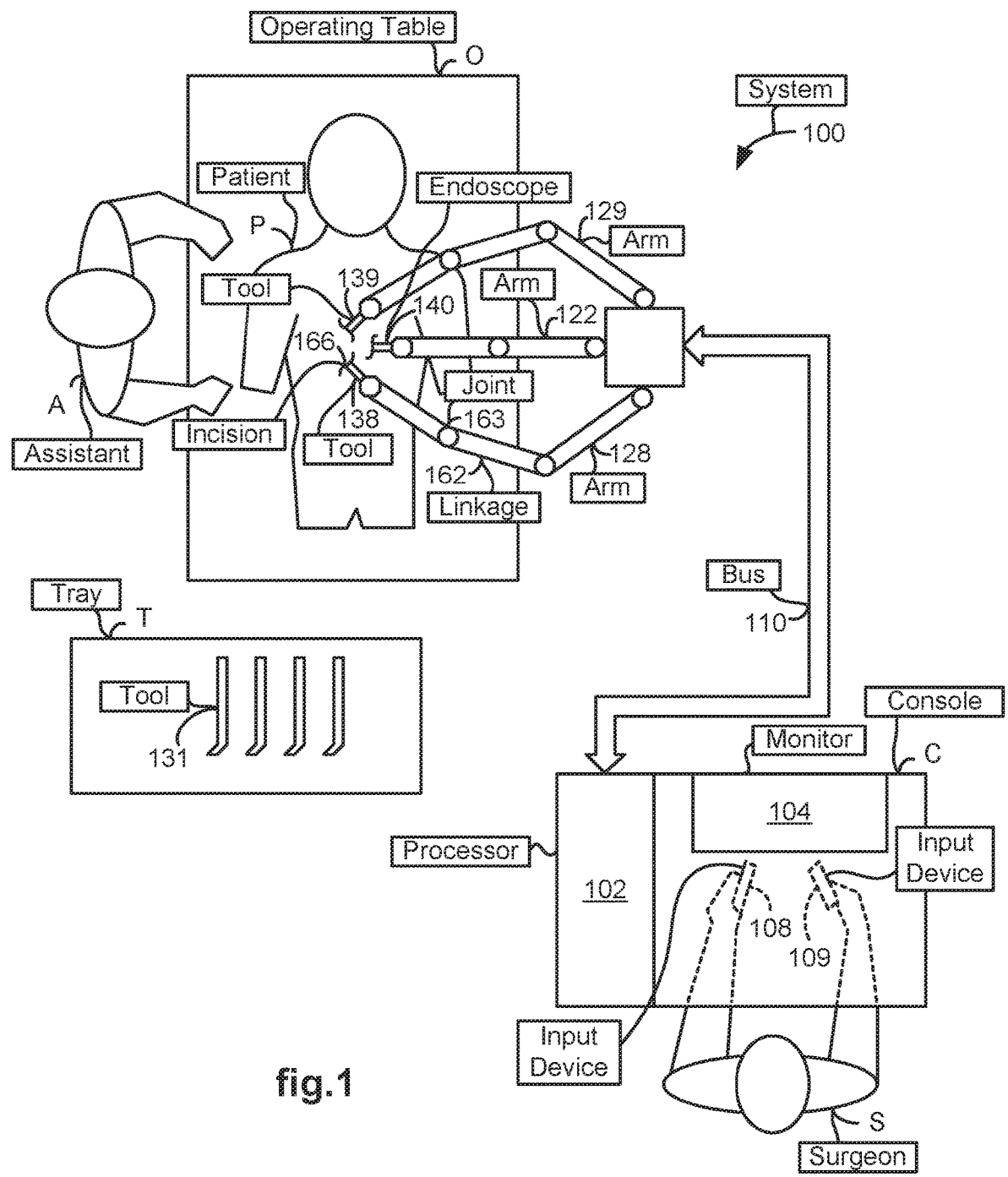
FIG. 1 illustrates a top view of an operating room employing a robotic surgical system utilizing aspects of the present invention.

FIG. 1 illustrates, as an example, a top view of an operating room employing a robotic surgical system. The robotic surgical system in this case is a Minimally Invasive Robotic Surgical (MIRS) system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a 3-D monitor 104 for displaying an image of a surgical site to the Surgeon, one or more manipulatable master manipulators 108 and 109 (also referred to herein as "control devices" and "input devices"), and a processor 102. The control devices 108 and 109 may include any one or more of a variety of input devices such as joysticks, gloves, trigger-guns, hand-operated controllers, or the like. The processor 102 is a personal computer that is integrated into the Console or positioned next to it.

The Surgeon performs a minimally invasive surgical procedure by manipulating the control devices 108 and 109 so that the processor 102 causes their respectively associated slave manipulators 128 and 129 (also referred to herein as "robotic arms" and "patient-side manipulators") to manipulate their respective removably coupled surgical instruments 138 and 139 (also referred to herein as "tools") accordingly, while the Surgeon views the surgical site in 3-D, as it is captured by a stereoscopic endoscope 140 (having left and right cameras for capturing left and right stereo views) and displayed on the Console 3-D monitor 104.

Each of the tools 138 and 139, as well as the endoscope 140, is preferably inserted through a cannula or other tool guide (not shown) into the Patient so as to extend down to the surgical site through a corresponding minimally invasive incision such as incision 166. Each of the robotic arms is conventionally formed of linkages, such as linkage 162, which are coupled together and manipulated through motor controlled joints, such as joint 163.

The number of surgical tools used at one time and consequently, the number of robotic arms being used in the system 100 will generally depend on the diagnostic or surgical procedure and the space constraints within the operating room, among other factors. If it is necessary to change one or more of the tools being used during a procedure, the Surgeon may instruct the Assistant to remove the tool no longer being used from its robotic arm, and replace it with another tool 131 from a Tray ("T") in the operating room. To aid the Assistant in identifying the tool to be replaced, each of the robotic arms 122, 128 and 129 may have an identifying number or color indicator printed on it, such as on its setup joint.

Preferably, the monitor 104 is positioned near the Surgeon's hands so that it will display a projected image that is oriented so that the Surgeon feels that he or she is actually looking directly down onto the operating site. To that end, an image of the tools 138 and 139 preferably appear to be located substantially where the Surgeon's hands are located. To do this, the processor 102 preferably changes the orientations of the control devices 108 and 109 so as to match the orientations of their associated tools 138 and 139 as seen by the endoscope 140.

The processor 102 performs various functions in the system 100. One important function that it performs is to translate and transfer the mechanical motion of control devices 108 and 109 to their respective robotic arms 128 and 129 through control signals over bus 110 so that the Surgeon can effectively move and/or manipulate their respective tools 138 and 139. Another important function is to implement a method for indicating positions of a tool when the tool is outside a camera captured view being displayed on the monitor 104, or occluded within the camera captured view being displayed on the monitor 104, as described herein. Still another important function is to implement a method for readily identifying tools and/or their respective patient-side manipulators on the monitor 104 to facilitate Surgeon/Assistant communications.

Although described as a personal computer, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

Figure 2:
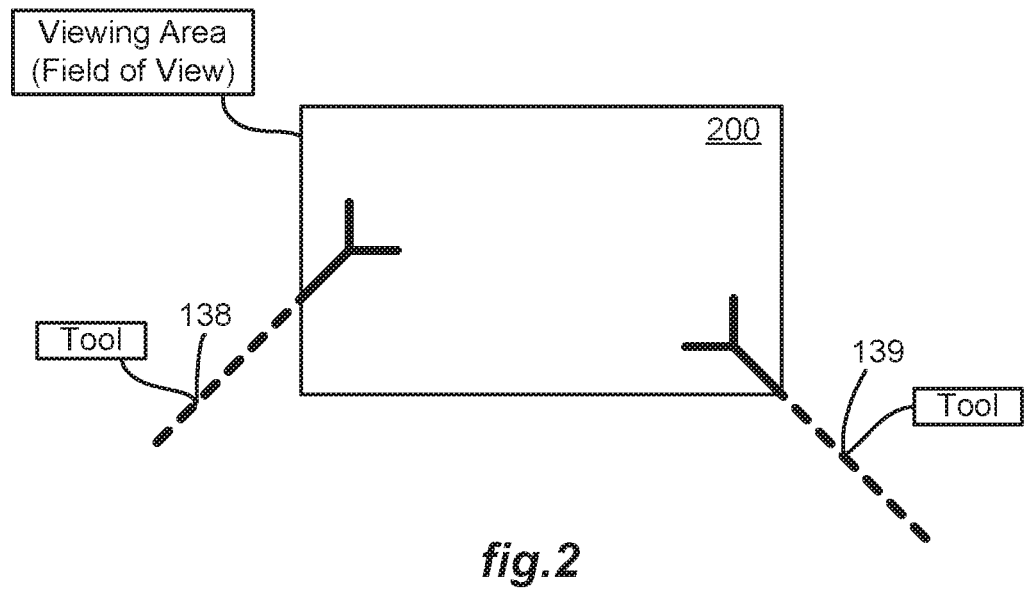
FIG. 2 illustrates two tools positioned in the FOV of an endoscope camera.
Figure 3:
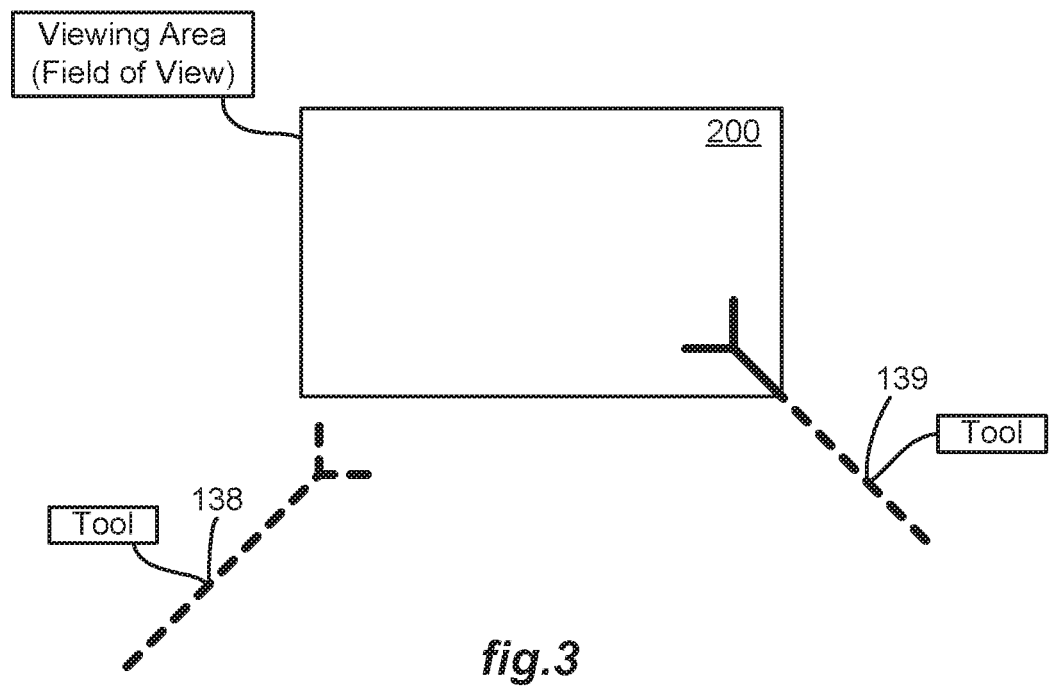
FIG. 3 illustrates one tool positioned in and one tool positioned out of the FOV of an endoscope camera.

During the performance of a minimally surgical procedure, the tools 138 and 139 are preferably kept within a viewing area 200 of the monitor 104 (such as shown in FIG. 2) so that the Surgeon may see them on the monitor 104 and accordingly, use them during the procedure. When one of the tools 138 is outside the viewing area 200 of the monitor 104 (such as shown in FIG. 3), however, the Surgeon will be unable to see that tool on the monitor 104 and consequently, will be unable to properly use it during the procedure. In addition, the Surgeon may have difficulty moving the out-of-view tool into the viewing area 200 of the monitor 104 without any knowledge of where the out-of-view tool is currently positioned relative to the viewing area 200.

Figure 7:
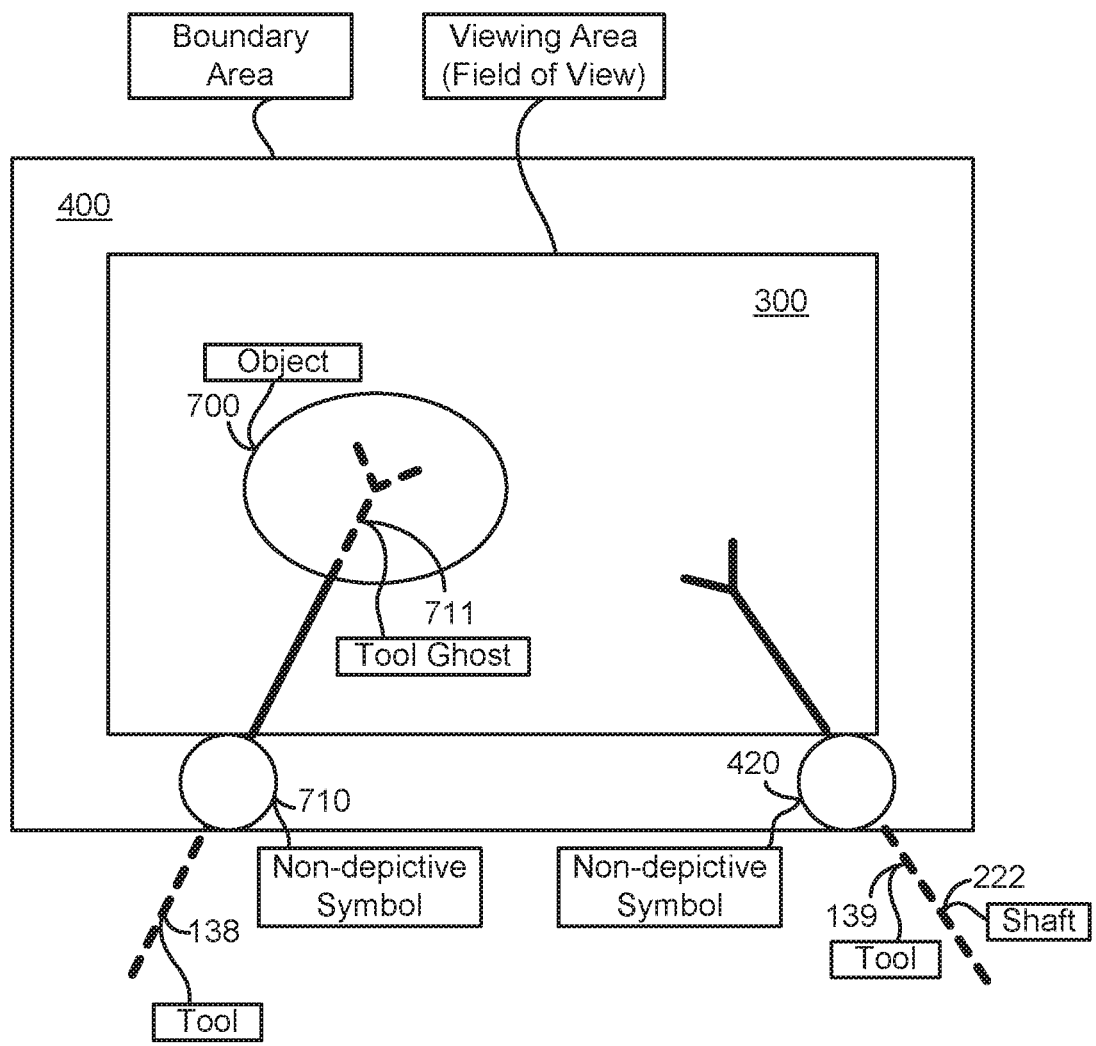
FIG. 7 illustrates a fourth computer display screen resulting from a method for indicating a tool's position when the tool is occluded in the FOV of an endoscope camera, utilizing aspects of the present invention.
Figure 8:
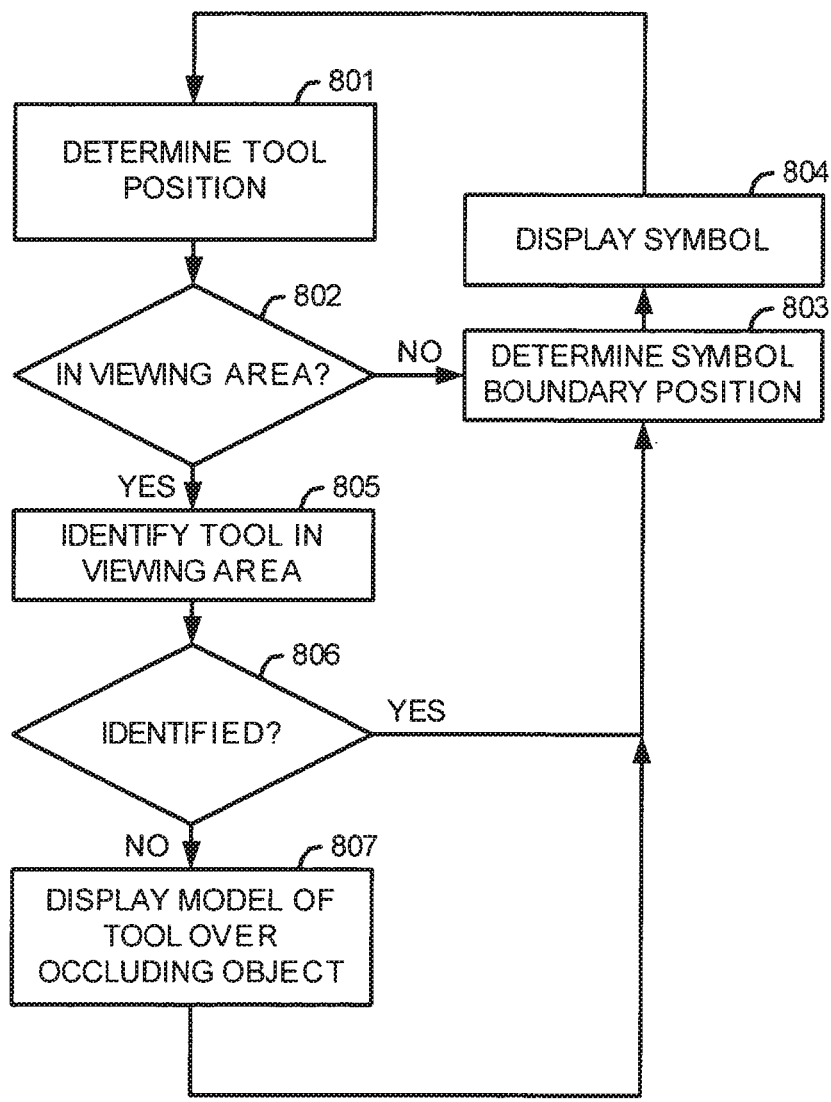
FIG. 8 illustrates a flow diagram of a method for indicating a tool's position when the tool is outside of, or occluded in, the FOV of an endoscope camera, utilizing aspects of the present invention.

To indicate tool positions to the Surgeon for out-of-view or occluded tools, the processor 102 is configured with a Graphical User Interface ("GUI") computer program which implements a method for indicating tool positions on the monitor 104, as described in reference to FIG. 8. Before describing this aspect of the GUI, however, examples of output generated by the GUI are illustrated and described in reference to FIGS. 4-7.

Figure 10:
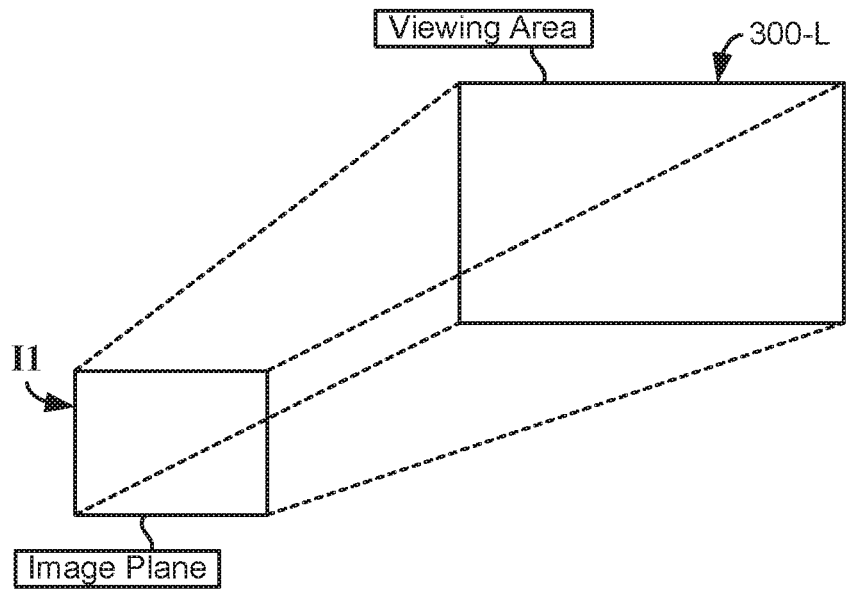
FIGS. 10 and 11 respectively illustrate a full left camera view being displayed on a left viewing area of a computer monitor and partial left camera view being displayed on a left viewing area of a computer monitor.
Figure 11:
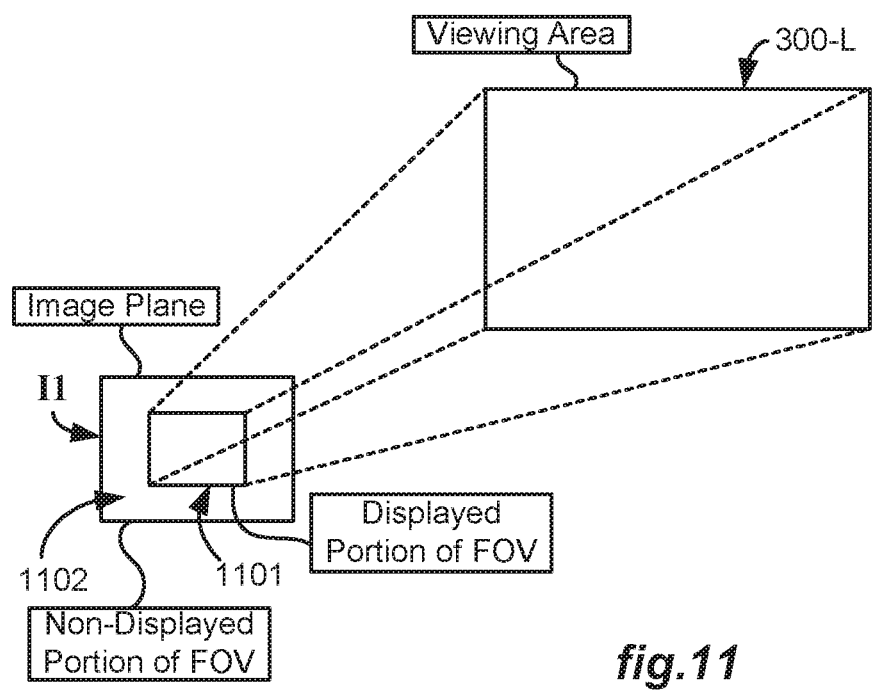

In each of the FIGS. 4-7, the viewing area 300 of the monitor 104 may correspond to the FOV of the endoscope 140 (with proper scaling of the entire FOV) such as depicted in FIG. 10, or it may correspond to only a portion of the FOV of the endoscope 140 (with proper scaling corresponding to a ZOOM-IN of images in the portion of the FOV displayed on the monitor 104) such as depicted in FIG. 11. Tools within the viewing area 300 are seen in bold line in the viewing area 300. Circumscribing the viewing area 300 is a boundary area 400, in which, non-clickable symbols or clickable icons (hereinafter cumulatively referred to as "symbols") are positioned so as to indicate positions of corresponding tools.

The symbols also preferably provide information identifying their respective tools and/or associated patient-side manipulators. One way they may do this is by their colors which may match color indications printed on the patient-side manipulators, such as on their setup joints. For example, patient-side manipulators 122, 128 and 129 may be color coded respectively as red, green and yellow, and symbols corresponding to their attached tools also color coded in the same manner. Alternatively, number indicators and/or other identifying information may be displayed on or adjacent to the symbols which may match numbers printed on the patient-side manipulators, such as on their setup joints. For example, patient-side manipulators 122, 128 and 129 may be numbered 1, 2 and 3 respectively, and symbols corresponding to their attached tools also numbered in the same manner. Where text information is provided with the symbols, the text may be written on or displayed adjacent to the symbol. It may be continuously displayed on the computer display screen, or only displayed when a cursor is placed over the symbol or the symbol is clicked on using a pointing device.

Tools outside the viewing area 300 are seen in dotted line for the purposes of explaining certain aspects of the method implemented by the GUI. It is to be appreciated that these dotted lined tools (or dotted line tool extensions) are not seen by the Surgeon on the monitor 104. Their relative positions with respect to the viewing area 300 in FIGS. 4-7, however, correspond to their relative positions in or to the FOV of the endoscope 140 in the endoscope camera frame of reference.

Although the tools shown in FIGS. 4-7 appear as 2-D images, it is to be appreciated that this is not to be construed as a limitation, but rather as a simplification for descriptive purposes only. Preferably, 3-D images are displayed in the viewing area 300. The symbols and in particular, end effector or tool shaft orientation indications superimposed on the symbols, may appear in 2-D or 3-D in the boundary area 400. Also, although the examples described herein refer to images captured by the endoscope 140, it is to be appreciated that the various aspects of the present invention are also applicable to images captured by other types of imaging devices such as those using Mill, ultrasound, or other imaging modalities, which may be displayed in the viewing area 300 of the monitor 104.

Figure 4:
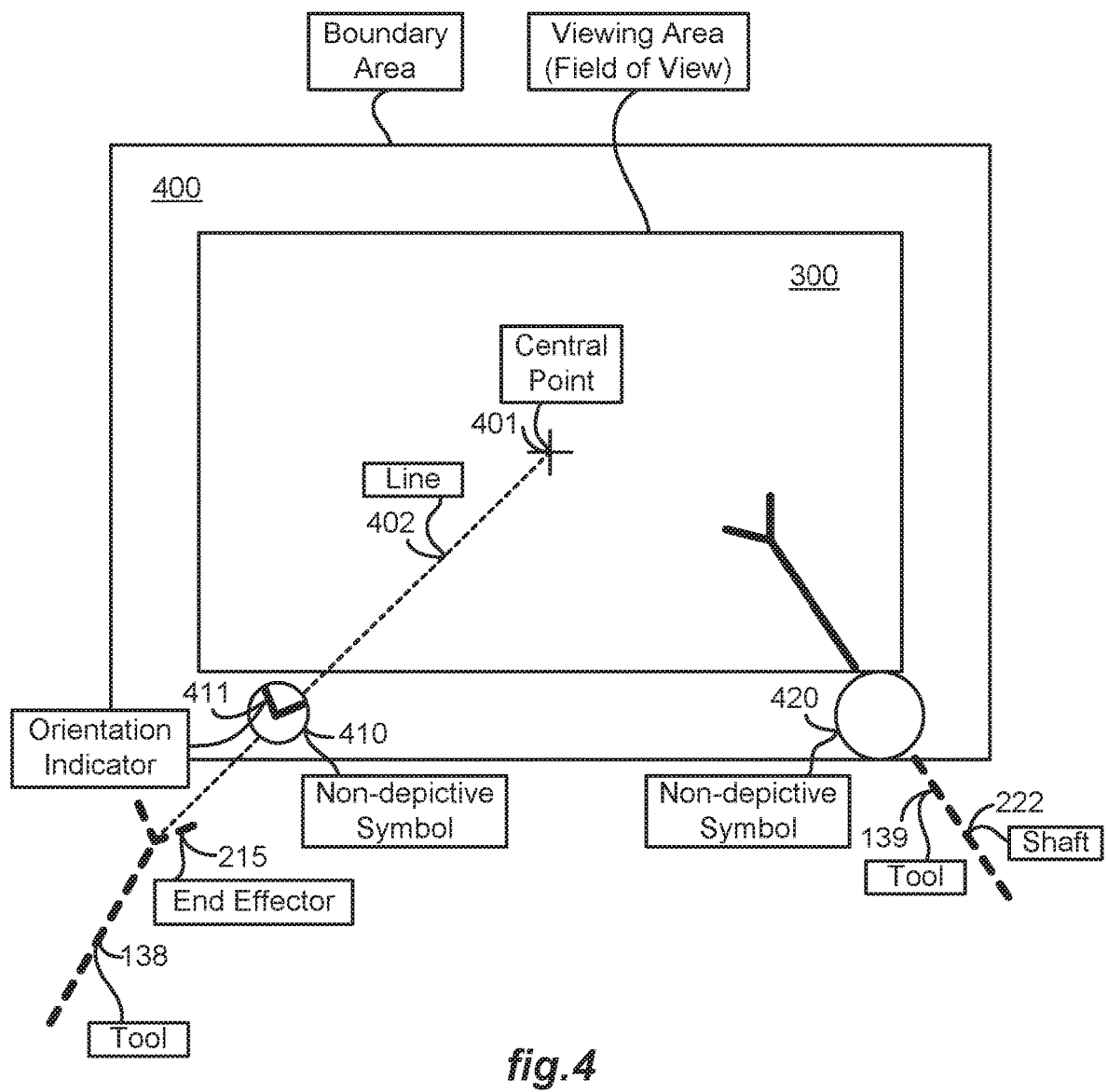
FIG. 4 illustrates a first computer display screen resulting from a method for indicating a tool's position when the tool is out of the FOV of an endoscope camera, utilizing aspects of the present invention.

FIG. 4 illustrates, as a first example, a GUI generated screen that is displayed on the monitor 104, wherein a first non-depictive symbol 410 is placed in the boundary area 400 to indicate the position of the out-of-view tool 138, and an orientation indicator 411 is superimposed on the symbol 410 to indicate the current orientation of an end effector 215 of the out-of-view tool 138, wherein the end effector 215 includes opposing members coupled to a shaft of the out-of-view tool 138. An in-view tool 139 is shown partially extending into the viewing area 300 from a second non-depictive symbol 420 in the boundary area 400. As used herein, the term "non-depictive symbol" means the symbol is non-depictive of its associated tool.

In this example, the position of the first symbol 410 is determined by the intersection of a line 402 and the boundary area 400, wherein the line 402 extends from a reference point on the out-of-view tool 138 to a central point 401 of the viewing area 300 of the monitor 104. The position of the second symbol 420 is determined by the intersection of the shaft 222 of the in-view tool 139 and the boundary area 400.

The distance that the out-of-view tool 138 is away from the viewing area 300, may be indicated in a number of ways, such as by the size, color, brightness/intensity, blinking frequency, or oscillating frequency of its symbol. Alternatively, the distance may be simply indicated by displaying a distance number (such as the distance in centimeters) over the symbol. For example, when the tool is in-view, such as the tool 139, then its symbol may be a maximum size, such as the symbol 420 of the in-view tool 139. When the tool is out-of-view, however, such as the tool 138, then the size of its symbol may indicate the distance that the out-of-view tool is away from the viewing area 300 so that it gets larger as the tool moves closer to entering the viewing area 300. Alternatively, the color of the symbol may indicate distance using a color spectrum, or the brightness/intensity of the symbol or the blinking frequency of the symbol may indicate distance by increasing as the tool moves closer to entering the viewing area 300, or an oscillation frequency of the symbol about its nominal position may reduce as the tool is brought closer to being in the viewing area 300.

Figure 5:
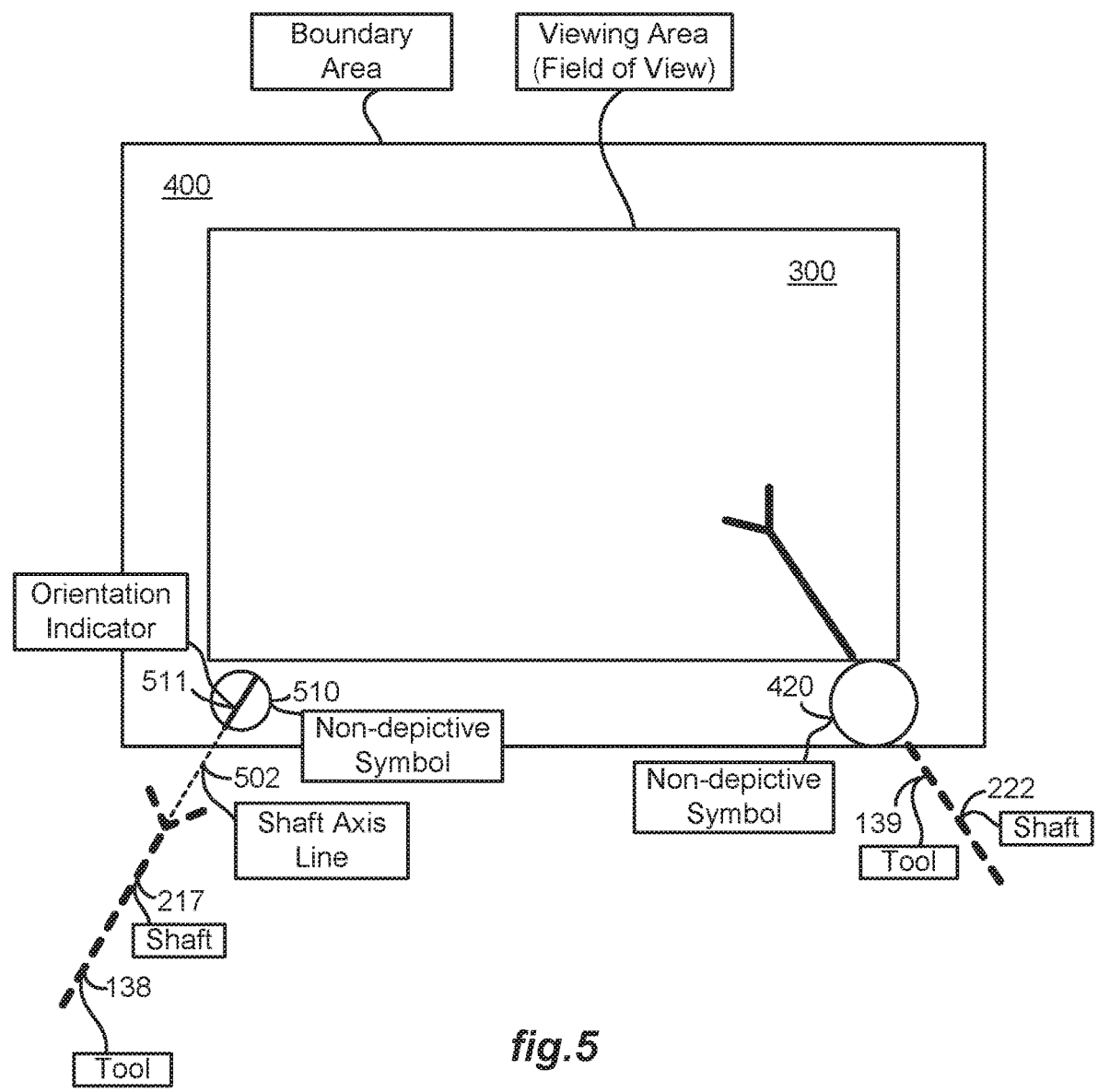
FIG. 5 illustrates a second computer display screen resulting from a method for indicating a tool's position when the tool is out of the FOV of an endoscope camera, utilizing aspects of the present invention.

FIG. 5 illustrates, as a second example, a GUI generated screen that is displayed on the monitor 104, wherein a first non-depictive symbol 510 is placed in the boundary area 400 to indicate the position of the out-of-view tool 138, and an orientation indicator 511 is superimposed on the symbol 510 to indicate the current orientation of a shaft 217 of the out-of-view tool 138.

In this example, the position of the first symbol 510 is determined by the intersection of a line 502 and the boundary area 400, wherein the line 502 extends along an axis of the shaft 217. The distance that the out-of-view tool 138 is away from the viewing area 300, may be indicated in the same manner as described above in reference to FIG. 4.

Figure 6:
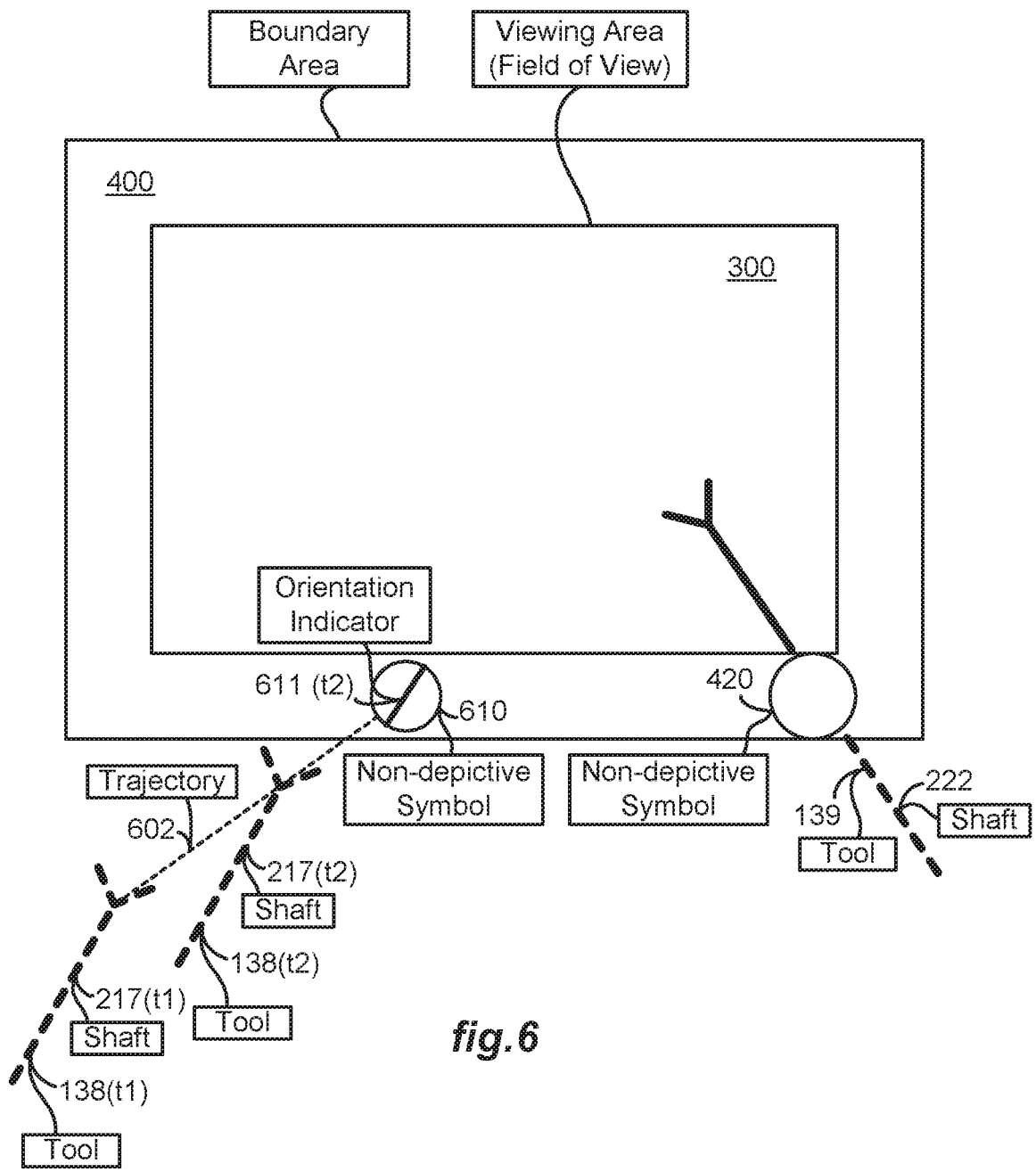
FIG. 6 illustrates a third computer display screen resulting from a method for indicating a tool's position when the tool is out of the FOV of an endoscope camera, utilizing aspects of the present invention.

FIG. 6 illustrates, as a third example, a GUI generated screen that is displayed on the monitor 104, wherein a first non-depictive symbol 610 is placed in the boundary area 400 to indicate the position of the out-of-view tool 138, and an orientation indicator 611 is superimposed on the symbol 610 to indicate the current orientation of a shaft 217 of the out-of-view tool 138.

In this example, the position of the first symbol 610 is determined by the intersection of a trajectory 602 and the boundary area 400, wherein the trajectory 602 is defined by the path of a reference point on the out-of-view tool 138 as it moves in the endoscope camera reference frame. In this way the symbol 610 is placed in the boundary area 400 where the tool will first appear in the viewing area 300 if it continues along its current trajectory (or, if it is moving away from the viewing area 300, where it would appear if the trajectory were reversed). For example, if only two points in time are used to determine the trajectory, as the tool 138 moves from a first location at time t1 to a second location at time t2, the path of the reference point is represented by a line extending through the two points. If time t2 is the current time and time t1 a prior time, then the current orientation of the shaft 217 is indicated by the orientation indicator 611. By using more than two points in time to define the trajectory of the out-of-view tool 138, the trajectory may take on more sophisticated curves. The distance that the out-of-view tool 138 is away from the viewing area 300, may be indicated in the same manner as described above in reference to FIG. 4.

FIG. 7 illustrates, as a fourth example, a GUI generated screen that is displayed on the monitor 104, wherein both tools 138 and 139 are positioned so as to be within the viewing area 300, but the end effector of the tool 138 is occluded by an object 700. In this case, since each of the tools is in the viewing area 300, their respective non-depictive symbols 710 and 420 are at maximum size. Although the end effector of the tool 138 is occluded by the object 700, a ghost image 711 (e.g., a computer model) of the end effector is shown at the proper position and orientation over the object 700. If the ghost image 711 is too distracting, then an outline of the end effector may be used instead, as either a programmed or surgeon selected option.

As previously described, the symbols 420, 410, 510, 610, and 710 may be non-clickable symbols or clickable icons. In the former case, if the Surgeon passes the cursor of a pointing device such as a mouse over the non-clickable symbol, additional information about the associated tool may be provided. In the latter case, if the Surgeon clicks on the clickable icon using the pointing device, additional information about the associated tool may be provided. The additional information in either case is information that is in addition to that identifying its associated patient-side manipulator, which may be indicated by its color or a number that is always displayed on or adjacent to the symbol. Examples of such additional information may include identification of the tool's type and its associated master manipulator. The additional information may be provided in a separate window such as a picture-in-picture, or it may be provided as text adjacent to, or superimposed over, the symbol. When the separate window is provided, the additional information may further include a zoomed out, computer generated view of the surgical site including the FOV of the endoscope 140 and computer generated models of all tools outside of it.

Although shown as circles, the non-depictive symbols 420, 410, 510, 610, and 710 may be displayed in any one or more of many different shapes. Alternatively, they may be displayed as depictive symbols, which are depictive of the respective tools, 138 and 139. For example, when the tool is positioned so as to be viewed inside the viewing area 300, then the symbol may be a depictive symbol that takes the form of a computer model of the tool shaft so that a ghost shaft is displayed in the boundary area 400. On the other hand, when the tool is positioned so as to be outside of the viewing area 300, then the symbol may be a depictive symbol that takes the form of a computer model of the distal end of the tool so that a ghost end effector is displayed in the boundary area 400. As the tool moves from outside of the viewing area 300 into the viewing area 300, the depictive symbol would then seamlessly change from the ghost end effector to the ghost shaft, and vice versa when the tool moves from inside of the viewing area 300 to outside of the viewing area 300. The orientation of the ghost shaft or ghost end effector, as the case may be, would preferably match that of the actual tool. When the tool is outside of the viewing area 300, the size of the ghost end effector may indicate its distance from the viewing area 300, as previously described for the non-depictive symbols. Likewise, in order to identify the tool and/or its patient-side manipulator, the ghost shaft or ghost end effector, as the case may be, may be color coded or numerically numbered as previously described for the non-depictive symbols.

FIG. 8 illustrates, as an example, a flow diagram of a method for indicating a tool's position and identification on the monitor 104. The method is preferably performed for each tool by a GUI executed in the processing unit 102. In 801, the position and orientation of a tool are determined in the reference frame of an imaging device whose captured images are being displayed on the monitor 104. Although for the purposes of this example the images are described as being captured by the stereo cameras of the endoscope 140, it is to be appreciated that images captured by other imaging devices using other imaging modalities may also be used with the method. Also for the purposes of this example, the full FOV of the cameras is assumed to be displayed in viewing area 300, such as depicted in FIG. 10. Therefore, in such case, the position and orientation of the tool may not be determinable using conventional imaging techniques when the tool is outside the FOV of the cameras.

Consequently, the tool position and orientation (also referred to herein as the "tool state") are first estimated in a tool reference frame by receiving information from joint sensors in the tool's robotic arm, and applying the information to kinematics of the robotic arm. Because the tool state in this case is primarily determined from the robotic arm kinematics, it can be readily determined even though the tool is outside the FOV of the endoscope 140 or occluded in the FOV of the endoscope 140.

The estimated tool state is then translated into the camera reference frame, and corrected using a previously determined error transform. The error transform may be determined from a difference between the tool state determined using its robotic arm kinematics and a tool state determined using video image processing. The error transform may be first determined with a pre-operative calibration step, and periodically updated when the tool is in the FOV of the endoscope 140 during a minimally invasive surgical procedure.

If only a portion of the FOV of the cameras is displayed in viewing area 300 of the monitor 104, however, such as depicted by area 1101 in FIG. 11, then it may still be possible to use conventional imaging techniques to determine the tool position if the tool is in a portion of the FOV of the cameras that is not being displayed in the viewing area 300 of the monitor 104, such as depicted by the area 1102 in FIG. 11. Note that in both FIGS. 10 and 11, only the left camera view I1 is shown. It is to be appreciated, however, that for a 3-D display, a corresponding right camera view I2 is also necessary as described, for example, in reference to FIG. 9, but is not being shown herein to simplify the description.

Additional details for determining tool positions and orientations, and in particular, for performing tool tracking are described, for example, in commonly owned U.S. application Ser. No. 11/130,471 entitled "Methods and Systems for Performing 3-D Tool Tracking by Fusion of Sensor and/or Camera derived Data during Minimally Invasive Robotic Surgery," file May 16, 2005, which is incorporated herein by this reference.

Figure 9:
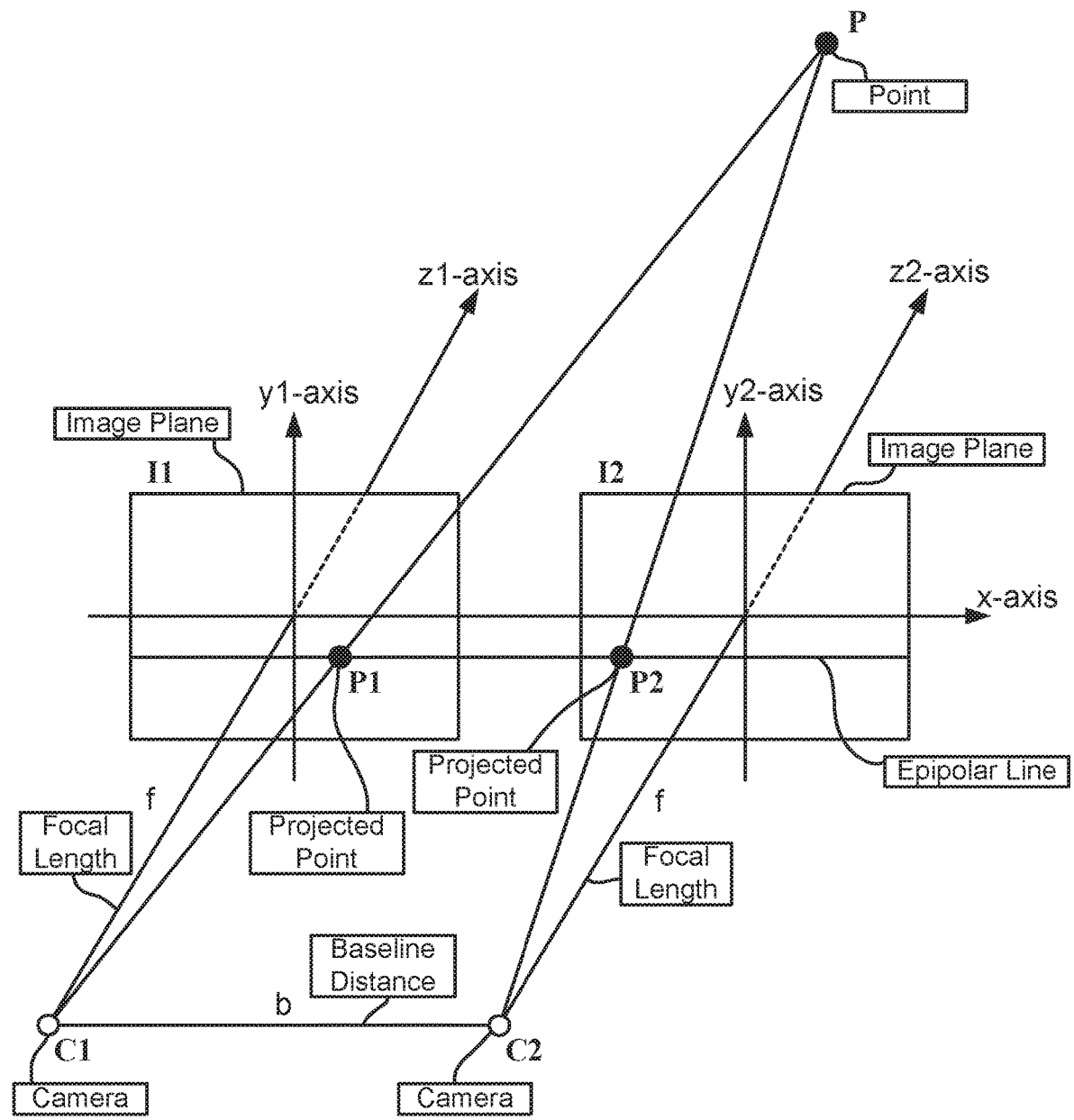
FIG. 9 illustrates left and right views of a point in an endoscope camera reference frame as used in a robotic surgical system configured to perform the method described in reference to FIG. 8 which utilizes aspects of the present invention.

In 802, a determination is made whether the position of the tool is within the viewing area 300 of the monitor 104, which is equivalent in this example to determining whether the tool is within the FOV of the endoscope 140. This latter determination may be performed using epipolar geometry. Referring to FIG. 9, for example, the endoscope 140 includes two cameras, C1 and C2, separated by a baseline distance "b", and having image planes, I1 and I2, defined at the focal length "f" of the cameras. The image planes, I1 and I2, are warped using a conventional stereo rectification algorithm to remove the effects of differing internal and external camera geometries.

A point P in the camera reference frame is projected onto the image planes, I1 and I2, at image points, P1 and P2, by an epipolar plane containing the point P, the two optical centers of the cameras, C1 and C2, and the image points, P1 and P2. The position of the point P may then be determined in the camera reference frame using known values for the baseline distance "b" and focal length "f", and a disparity "d" calculated from the distances of the image points, P1 and P2, from their respective image plane center points (i.e., at the intersections of the x-axis with the y1 and y2 axes).

Thus, in order for a tool to be in the FOV of the endoscope 140, at least one point on the tool must be projected onto at least one of the two image planes, I1 and I2. Although it may be possible to estimate a position of a point on the tool that is projected onto only one of the two image planes, I1 and I2, using disparity information calculated for nearby points, for example, preferably the point on the tool would be projected onto both of the two image planes, I1 and I2, so that a disparity value may be calculated for the point and consequently, its depth can be determined directly. Also, although the tool may technically be in the FOV of the endoscope 140 if only one point of the tool is in it, for practical reasons, a sufficient number of points are preferably required so that the tool is visually identifiable in the monitor 104 by the Surgeon.

Now, if the position of the tool is determined in 802 to be outside the viewing area 300 of the monitor 104, then in 803, a position for a symbol in the boundary area 400 circumscribing the viewing area 300 is determined such that the position of the symbol indicates the tool's position relative to the viewing area 300. Examples of such determination have been previously described in reference to FIGS. 4-6. After determining the position of the symbol in the boundary area 400, in 804, the symbol is then displayed in the boundary area 400 at its determined position. In addition, an orientation indicator may be superimposed on the symbol and other tool and/or its robotic arm identifying information provided as described in reference to FIGS. 4-6. The method then repeats for another processing interval by going back to 801.

Figure 12:
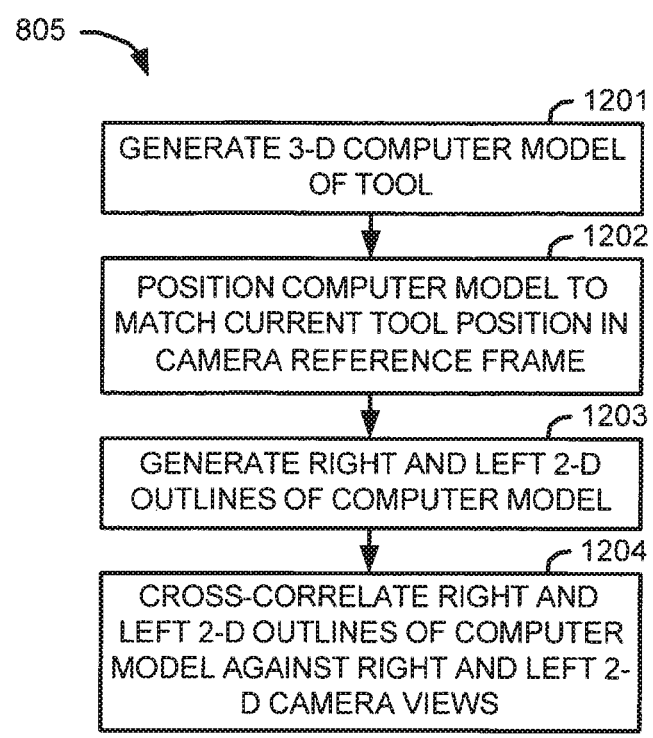
FIG. 12 illustrates a flow diagram of a method for identifying a tool in a camera view that may be used in the method described in reference to FIG. 8 which utilizes aspects of the present invention.

On the other hand, if the position of the tool is determined in 802 to be within the viewing area 300 of the monitor 104, then in 805, an attempt is made to identify the tool in the FOV of the endoscope 140. Referring to FIG. 12 as one example for performing this task, in 1201, a 3-D computer model of the tool is generated. This is generally a one time, pre-operative process. In 1202, the 3-D computer model of the tool is positioned and oriented according to the tool state determined in 801. In 1203, right and left 2-D outlines of the computer model of the tool are generated by projecting an outline of the 3-D computer model of the tool onto the left and right image planes, I1 and I2, of the left and right cameras, C1 and C2, of the endoscope 140. In 1204, the 2-D outline of the computer model of the tool that was generated in 1203 for the left image plane I1 is cross-correlated with a left camera view captured by the left camera C1, and/or the 2-D outline of the computer model of the tool that was generated in 1203 for the right image plane I2 is cross-correlated with a right camera view captured by the right camera C2.

In 806, a determination is then made whether the tool has been identified in the FOV of the endoscope 140 by, for example, determining whether a cross-correlation value calculated in 1204 meets or exceeds a threshold value for one or both of the left and right camera views. If the result of 806 is a YES, then the tool has been identified in the right and/or left camera view. The method then goes to 803 to determine the symbol position in the boundary area 400, which in this case may be simply determined by the intersection of the tool shaft with the boundary area 400. The method then proceeds to 804 to display the symbol in the determined position in the boundary area 400, and then to 801 to repeat the method for another processing period.

If the result of 806 is a NO, however, then the tool is presumably occluded by another object. In that case, in 807, the 2-D outline of the computer model of the tool that was generated by projecting the 3-D computer model of the tool into the left image plane I1 is superimposed on the left camera view captured by the left camera C1, and the 2-D outline of the computer model of the tool that was generated by projecting the 3-D computer model of the tool into the right image plane I2 is superimposed on the right camera view captured by the right camera C2. As a result, a 3-D outline of the computer model of the tool is displayed in the viewing area 300 of the monitor 104 superimposed over the occluding object. Alternatively, the full 3-D computer model of the tool may be displayed as a ghost tool rather than just its outline over the occluding object by superimposing appropriate left and right images of the 3-D computer model on the left and right camera views captured by the cameras C1 and C2 of the endoscope 140.

The method then goes to 803 to determine the symbol position in the boundary area 400, which in this case may be simply determined by the intersection of the tool shaft with the boundary area 400. The method then proceeds to 804 to display the symbol in the determined position in the boundary area 400, and then to 801 to repeat the method for another processing period.

Although the various aspects of the present invention have been described with respect to a preferred embodiment, it will be understood that the invention is entitled to full protection within the full scope of the appended claims.

What is claimed is:

1. An apparatus comprising:
   a memory device non-transitorily storing program instructions; and
   a processor coupled to a display device, an image capture device, and the memory device, the processor configured to execute the program instructions to:
   cause images captured by the image capture device to be displayed in a viewing area on the display device;
   determine a position of a tool in a reference frame of the image capture device, wherein the tool has a shaft and an end effector including opposing members coupled to the shaft;
   determine a position to display a non-depictive symbol for the tool in a boundary area circumscribing the viewing area on the display device so as to indicate a direction of the determined position of the tool relative to a field of view of the image capture device, by determining a trajectory of the tool from current and past positions of the tool and by determining where an extrapolation of the trajectory enters the field of view of the image capture device, wherein the non-depictive symbol for the tool does not resemble the end effector of the tool in appearance, and wherein the position of the non-depictive symbol for the tool in the boundary area does not indicate a distance of the tool from the field of view of the image capture device; and cause the non-depictive symbol for the tool to be displayed at the determined position in the boundary area while images that were captured by the image capture device are restricted to being displayed in the viewing area on the display device.

2. The apparatus according to claim 1, wherein the processor is further configured to execute the program instructions to:

cause the non-depictive symbol for the tool to be displayed at the determined position in the boundary area so that the non-depictive symbol for the tool provides information identifying one of: the tool or a manipulator used for moving the tool.

3. The apparatus according to claim 2, wherein the processor is further configured to execute the program instructions to:

cause the non-depictive symbol for the tool to be displayed at the determined position in the boundary area so that the non-depictive symbol for the tool is marked with one of: a color that is uniquely associated with the manipulator or a number that is uniquely associated with the manipulator.

4. The apparatus according to claim 2, wherein the processor is further configured to execute the program instructions to:

determine the position of the tool by using kinematics for the manipulator.

5. The apparatus according to claim 1, wherein the processor is further configured to execute the program instructions to:

cause the non-depictive symbol for the tool to be displayed at the determined position in the boundary area by:

determining a distance of a position of a reference point on the tool from a position of a reference point in the field of view of the image capture device; and causing the non-depictive symbol for the tool to be displayed so that its size indicates the distance.

6. The apparatus according to claim 1, wherein the processor is further configured to execute the program instructions to:

cause the non-depictive symbol for the tool to be displayed at the determined position in the boundary area by:

determining a distance of a position of a reference point on the tool from a position of a reference point in the field of view of the image capture device; and causing the non-depictive symbol for the tool to be displayed so that its color indicates the distance.

7. The apparatus according to claim 6, wherein the processor is further configured to execute the program instructions to:

cause the non-depictive symbol for the tool to be displayed in the boundary area so that intensity of the color of the non-depictive symbol for the tool indicates the distance.

8. The apparatus according to claim 6, wherein the processor is further configured to execute the program instructions to:

cause the non-depictive symbol for the tool to be displayed in the boundary area so that the color of the non-depictive symbol for the tool relative to a color spectrum indicates the distance.

9. The apparatus according to claim 1, wherein the processor is further configured to execute the program instructions to:

cause the non-depictive symbol for the tool to be displayed at the determined position in the boundary area by:

determining a distance of a position of a reference point on the tool from a position of a reference point in the field of view of the image capture device; and causing the non-depictive symbol for the tool to be displayed so that a frequency of blinking of the non-depictive symbol for the tool indicates the distance.

10. The apparatus according to claim 1, wherein the processor is further configured to execute the program instructions to:

cause the non-depictive symbol for the tool to be displayed at the determined position in the boundary area by:

determining a distance of a position of a reference point on the tool from a position of a reference point in the field of view of the image capture device; and causing the non-depictive symbol for the tool to be displayed so that a frequency of oscillation of the non-depictive symbol for the tool about the determined position in the boundary area indicates the distance.

11. The apparatus according to claim 1, wherein the processor is further configured to execute the program instructions to:

cause the non-depictive symbol for the tool to be displayed at the determined position in the boundary area by:

determining a distance of a position of a reference point on the tool from a position of a reference point in the field of view of the image capture device; and causing the non-depictive symbol for the tool to be displayed so that the distance is indicated by overlaying a distance number over the non-depictive symbol for the tool.

12. The apparatus according to claim 1, wherein the processor is further configured to execute the program instructions to:

determine the position of the tool by determining a position and an orientation of the end effector of the tool, and cause the non-depictive symbol for the tool to be displayed at the determined position in the boundary area by causing an orientation indicator to be displayed over the non-depictive symbol for the tool such that the orientation indicator is oriented so as to indicate the orientation of the end effector.

13. The apparatus according to claim 1, wherein the processor is further configured to execute the program instructions to:

determine an orientation of an axis that extends along a length of a shaft of the tool, and cause the non-depictive symbol for the tool to be displayed at the determined position in the boundary area by causing an orientation indicator to be displayed over the non-depictive symbol for the tool such that the orientation indicator is oriented so as to indicate the orientation of the axis.

* * * * *